(12) United States Patent
Bowden et al.

(10) Patent No.: US 8,093,252 B2
(45) Date of Patent: Jan. 10, 2012

(54) CRYSTALLINE POLYMORPHIC FORM OF GLUCOKINASE ACTIVATOR

(75) Inventors: Sharon Ann Bowden, Bristol (GB); David Peter Hoile, Bristol (GB); Karin Lövqvist, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/705,710

(22) Filed: Feb. 15, 2010

(65) Prior Publication Data

US 2010/0210621 A1  Aug. 19, 2010

(30) Foreign Application Priority Data

Feb. 13, 2009  (GB) .................................. 0902406.8

(51) Int. Cl.
*A61K 31/4965* (2006.01)
(52) U.S. Cl. .................... 514/255.06; 544/408; 548/953
(58) Field of Classification Search ............. 514/255.06; 544/408; 548/953
See application file for complete search history.

(56) References Cited

U.S. PATENT DOCUMENTS

| | | |
|---|---|---|
| 2,750,393 A | 6/1956 | Elpern |
| 2,967,194 A | 1/1961 | Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,255,335 B1 | 7/2001 | Himmler et al. |
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 7,390,908 B2 | 6/2008 | Boyd et al. |
| 7,524,957 B2 | 4/2009 | Boyd et al. |
| 7,642,259 B2 | 1/2010 | McKerrecher et al. |
| 7,642,263 B2 | 1/2010 | McKerrecher et al. |
| 7,671,060 B2 | 3/2010 | Martin et al. |
| 7,696,191 B2 | 4/2010 | McCabe et al. |
| 7,700,640 B2 | 4/2010 | Cornwall et al. |
| 7,709,505 B2 | 5/2010 | McKerrecher et al. |
| 7,745,475 B2 | 6/2010 | Johnstone et al. |
| 7,902,200 B2 | 3/2011 | Campbell et al. |
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |
| 2003/0228982 A1 | 12/2003 | Helmke et al. |
| 2004/0014968 A1 | 1/2004 | Bizzarro et al. |
| 2004/0077555 A1 | 4/2004 | Ishihara et al. |
| 2004/0214868 A1 | 10/2004 | Hayter et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0058353 A1 | 3/2006 | Mckerrecher et al. |
| 2006/0167053 A1 | 7/2006 | Iino et al. |
| 2006/0258728 A1 | 11/2006 | Tani et al. |
| 2007/0078168 A1 | 4/2007 | Caulkett |
| 2007/0093535 A1 | 4/2007 | Hayter et al. |
| 2007/0112040 A1 | 5/2007 | Hayter et al. |
| 2007/0255062 A1 | 11/2007 | Johnstone et al. |
| 2007/0287693 A1 | 12/2007 | Johnstone et al. |
| 2008/0015203 A1 | 1/2008 | Johnstone et al. |
| 2008/0057074 A1 | 3/2008 | Takaoka et al. |
| 2008/0153800 A1 | 6/2008 | McCabe et al. |

(Continued)

FOREIGN PATENT DOCUMENTS

CA          2605738          11/2006

(Continued)

OTHER PUBLICATIONS

Alvarez et al. "Evidence that glucokinase regulatory protein is expressed and interacts with glucokinase in rat brain" J. Neurochem. 80(1):45-53 (2002).

(Continued)

*Primary Examiner* — James O Wilson
*Assistant Examiner* — Douglas M Willis
(74) *Attorney, Agent, or Firm* — Morgan Lewis & Bockius LLP

(57) ABSTRACT

A new polymorphic form of 3-{[5-(azetidin-1-ylcarbonyl)pyrazin-2-yl]oxy}-5-{[(1S)-1-methyl-2-(methyloxy)ethyl]oxy}-N-(5-methylpyrazin-2-yl)benzamide, processes for making it and its use as an activator of glucokinase are described.

7 Claims, 12 Drawing Sheets

U.S. PATENT DOCUMENTS

| | | |
|---|---|---|
| 2008/0171734 A1 | 7/2008 | Campbell et al. |
| 2008/0200694 A1 | 8/2008 | Cornwall et al. |
| 2008/0234273 A1 | 9/2008 | McKerrecher et al. |
| 2008/0280872 A1 | 11/2008 | Johnstone et al. |
| 2008/0280874 A1 | 11/2008 | Johnstone et al. |
| 2008/0300412 A1 | 12/2008 | Hopes et al. |
| 2008/0312207 A1 | 12/2008 | Johnstone et al. |
| 2008/0318968 A1 | 12/2008 | Martin et al. |
| 2009/0018157 A1 | 1/2009 | Johnstone et al. |
| 2009/0029905 A1 | 1/2009 | Mckerrecher et al. |
| 2009/0062351 A1 | 3/2009 | Caulkett et al. |
| 2009/0105214 A1 | 4/2009 | McKerrecher et al. |
| 2009/0105263 A1 | 4/2009 | Caulkett et al. |
| 2009/0111790 A1 | 4/2009 | Mckerrecher et al. |
| 2009/0118159 A1 | 5/2009 | McKerrecher et al. |
| 2009/0227592 A1 | 9/2009 | Boyd et al. |
| 2009/0253676 A1 | 10/2009 | Johnstone et al. |
| 2009/0264336 A1 | 10/2009 | Mckerrecher et al. |
| 2010/0093757 A1 | 4/2010 | Bennett et al. |
| 2010/0094009 A1 | 4/2010 | McCabe et al. |
| 2010/0160286 A1 | 6/2010 | Mckerrecher et al. |
| 2010/0173825 A1 | 7/2010 | Martin et al. |
| 2010/0210841 A1 | 8/2010 | Butters et al. |
| 2010/0261704 A1 | 10/2010 | Waring |
| 2011/0034432 A1 | 2/2011 | Johnstone et al. |
| 2011/0053910 A1 | 3/2011 | Mckerrecher et al. |
| 2011/0059941 A1 | 3/2011 | Caulkett et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1790637 | 5/2005 |
| EP | 1541563 | 6/2005 |
| EP | 1600442 | 11/2005 |
| EP | 1604981 | 12/2005 |
| EP | 1702919 | 9/2006 |
| EP | 1995246 | 11/2008 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |

| | | |
|---|---|---|
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/105637 | 9/2007 |
| WO | WO 2008/050101 | 5/2008 |
| WO | WO 2008/050117 | 5/2008 |
| WO | WO 2008/075073 | 6/2008 |

OTHER PUBLICATIONS

Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the pyrido[2,3-d]pyrimidine series" J. Org. Chem. 42(6):993-996 (1977).
Ando et al. "Fluoride salts on alumina as reagents for alkylation of phenols and alcohols" Bull. Chem. Soc. Jpn. 55(8):2504-2507 (1982).
Atwell et al. "Potential antitumor agents. VI. Bisquaternary salts" J. Med. Chem. 11(2):295-300 (1968).
Baker et al. "Structure and synthesis of Pallescansin E utilising a modified Wadsworth-Emmons reaction" J. Chem. Soc., Perkin Trans. 1, 12:3087-3091 (1981).
Baker et al. "Synthesis of Pallescensin-E: Use of crown ether in the Wadsworth procedure for olefin formation" Tetrahedron Letters 22:161-162 (1981).
Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry No. 6511458 (Apr. 18, 1994) [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42(22):3514-3518 (1977).
Berl et al. "Induced fit selection of a barbiturate receptor from a dynamic structural and conformational/ configurational library" European J. Org. Chem. (11):3089-3094 (1999).
Berl et al. "Template-induced and molecular recognition directed hierarchical generation of supramolecular assemblies from molecular strands" Chem. Eur. J. 6(11):1938-1946 (2000).
Bonina et al. "Synthesis and pharmacologic activity of 2-arylethenylthiazol-4-acetic and 4-carboxylic acids" II Farmaco 40(11):875-884 (1985).
Boucherle et al. "Recherches dans la serie des cetones polyphenoliques IV. Thiazoles" Chimica Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13 Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caira "Crystalline polymorphism of organic compounds" Topics in Current Chemistry 198:163-208 (1998).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2011).
Chemical Abstracts Service, Columbus, Ohio, US: CAS Registry No. 354767-66-1 (Sep. 5, 2001).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Christesen et al. "The second activating glucokinase mutation (A456V): Implications for glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coghlan et al. "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo—and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22:1686 (1957).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—a glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methyl-morpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel anti-diabetic agents" Biochemical Society Transactions 33(Part 2):371-374 (2005).

Leighton, "Pre-clinical disease models—challenges and success stories"44th Drug Information Association Annual Meeting, Boston, MA, US (2008).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).
Levin et al. "Differential effects of diet and obesity on high and low affinity sulfonylurea binding sites in the rat brain" Brain Research 739(1-2):293-300 (1996).
Levin et al. "In vivo and in vitro regulation of [3H]glyburide binding to brain sulfonylurea receptors in obesity-prone and resistant rats by glucose" Brain Research 776(1-2):146-153 (1997).
Levin et al. "Reduced glucose-induced neuronal activation in the hypothalamus of diet-induced obese rats" Brain Research 808(2):317-319 (1998).
Levkoev et al. "Research on cyanide dyes 11. 7,7'-Dimethylthiacarbocyanines" Zhurnal Obshchei Khimii 27:3097-3107 (1957) (Translation enclosed).
Lith, "Evaluation of the effects on whole body glucose metabolism after single doses of X2000—A glucose lowering agent" Poster presentation, Master thesis in Pharmaceutical Bioscience, Goteborgs University (2008).
Lynch et al. "Localization of glucokinase gene expression in the rat brain" Diabetes 49(5):693-700 (2000).
Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).
Mastafanova et al. "Synthesis and study of the antihypertensive activity of substituted N-acetylmercaptopropionyl-6[2'-phenylethyl]pipecolinic acids" Khimiko Farmatsevticheskii Zhurnal 22(3):294-302 (1988).
Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).
Mazik et al. "Molecular recognition of carbohydrates by artificial polypyridine and polypyrimidine receptors" Angewandte Chemie International Edition 39(3):551-554 (2000).
Mazik et al. "Molecular recognition of carbohydrates by artificial receptors: systematic studies towards recognition motifs for carbohydrates" Chem. Eur. J. 7(3):664-670 (2001).
McKerrecher "Design and synthesis of novel glucokinase activators" 13th RSC-SCI Medicinal Chemistry Symposium, Churchill College, Cambridge (Sep. 4-7, 2005).
McKerrecher et al. "Design & synthesis of novel glucokinase activators as potential treatments for type 2 diabetes" 233rd ACS National Meeting, Chicago, IL (Mar. 25-29, 2007).
McKerrecher et al. "Design and synthesis of novel glucokinase activators as potential treatment for type 2 diabetes" Frontiers in Medicinal Chemistry, Frankfurt (Mar. 12-15, 2006).
McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.
McKerrecher et al. "Discovery, synthesis and biological evaluation of novel glucokinase activators" Bioorg Med Chem Left. 15(8):2103-2106 (2005).
McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).
McKerrecher et al. "Identification of orally bioavailable small molecule activators of glucokinase" Abstract, Anglo-Swedish Medicinal Chemistry Meeting (Mar. 2005).
Meijer et al "Chiral amplification in supramolecular stacks" Polymer Preprints 41(1):902-903 (2000).
Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).
Moore et al. "Acute fructose administration improves oral glucose tolerance in adults with type 2 diabetes" Diabetes Care 24(11):1882-1887 (2001).
Motesharei et al. "Molecular recognition in membrane mimics: A fluorescence probe" J. Am. Chem. Soc. 116(16):7413-7414 (1994).
Motesharei et al. "Molecular recognition on functionalized self-assembled monolayers of alkanethiols on gold" J. Am. Chem. Soc. 120(29): 7328-7336 (1998).
Palmans "Extended-core discotic liquid crystals based on the intramolecular H-bonding in N-acylated 2,2'-bipyridine-3,3'-diamine moieties" Chem. Eur. J. 3(2):300-307 (1997).
Plieninger et al. "Synthesis of 7,8-dihydro-5,6-benzoquinoline-(3)-carboxylic acid" Chemische Berichte 87:882-887 (1954) (Translation enclosed).
Printz et al. "Mammalian glucokinase" Annu. Rev. Nutr. 13:463-496 (1993).
Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).
Qian-Cutrone et al. "Glucolipsin A and B, two new glucokinase activators produced by *Streptomyces purpurogeniscleroticus* and *Nocardia vaccinii*" Journal of Antibiotics (Tokyo), 52(3):245-255 (1999).
Ralph et al. "Glucose Modulation of Glucokinase Activation by Small Molecules" Biochemistry 47(17):5028-5036 (2008).
Rivalle et al. "2,3 Disubstituted furans and pyrroles—XVIII: Synthesis annd rearrangement of 4H-dihydro-9,10 benzo[4,5]cyclohepta[1,2-b]furannones-4" Tetrahedron 32(7):829-834 (1976).
Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).
Rogers et al. "Mesoionic purinone analogues as inhibitors of cyclic-AMP phosphodiesterase: a comparison of several ring systems" J. Med. Chem. 24(11):1284-1287 (1981).
Roncero et al. "Functional glucokinase isoforms are expressed in rat brain" J. Neurochem. 74(5):1848-1857 (2000).
Rowe et al. "Potassium channel dysfunction in hypothalamic glucose-receptive neurones of obese Zucker rats" Journal of Physiology 497.2:365-377 (1996).
Sarabu et al., "Glucokinase activators as new type 2 diabetes therapeutic agents" Expert Opinion on Therapeutic Patents 18(7):759-768 (2008).
Schuit et al. "Glucose sensing in pancreatic β-Cells. A model for the study of other glucose-regulated cells in gut, pancreas, and hypothalamus" Diabetes 50:1-11 (2001).
Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).
Seoane et al. "Glucokinase overexpression restores glucose utilization and storage in cultured hepatocytes from male Zucker diabetic fatty rats" J Biol Chem. 274(45):31833-31838 (1999).
Shiota et al. "Glucokinase gene locus transgenic mice are resistant to the development of obesity-induced type 2 diabetes" Diabetes 50(3):622-629 (2001).
Shorvon, "Pyrrolidone derivatives" Lancet 358(9296):1885-1892 (2001).
Spanswick et al. "Insulin activates ATP-sensitive K+ channels in hypothalamic neurons of lean, but not obese rats" Nature Neuroscience 3(8):757-758 (2000).
Spanswick et al. "Leptin inhibits hypothalamic neurons by activation of ATP-sensitive potassium channels" Nature 390(6659):521-525 (1997).
Stout et al. "Synthesis and antiarrhythmic and parasympatholytic properties of substituted phenols. 3. Modifications to the linkage region (region 3)" J. Med. Chem. 28(3):295-298 (1985).
Suhua et al. "Synthesis and biological activity of tyrosine protein kinase inhibitors" Acta Pharmaceutica Sinica 32(7): 515-523 (1997).
Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984).

Tecilla et al. "Hydrogen-bonding self-assembly of multichromophore structures" J. Am. Chem. Soc. 112:9408-9410 (1990).
Tecilla et al. "Synthetic hydrogen bonding receptors as models of transacylase enzymes" Tetrahedron 51(2):435-448 (1995).
Tecilla et al. "Transition-state stabilization and molecular recognition: acceleration of phosphoryl-transfer reactions by an artificial receptor" J. Am. Chem. Soc. 112:9586-9590 (1990).
Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).
Tucker et al. "Novel Inhibitors of prolyl 4-hydroxylase. 2. 5-amide substituted pyridine-2-carboxylic acids" J. Med. Chem. 3(5)5:804-807 (1992).
Van Gorp et al. "C3-symmetrical supramolecular architectures: fibers and organic gels from discotic trisamides and trisureas" J Am. Chem. Soc. 124(49):14759-14769 (2002).
Vanderstelt et al. "Synthesis and pharmacological properties of some derivatives of 5H-benzo[4,5]cyclohepta[1,2-b] pyridine and of 11H-benzo[5,6] cyclohepta[1,2-c] pyridine III" Arzneim. Forsch. 22(1):133-137 (1972).
Velho et al. "Impaired hepatic glycogen synthesis in glucokinase-deficient (MODY-2) subjects" J. Clin. Invest. 98(8):1755-1761 (1996).
Vertigan et al. "Impact of cell glycogen content on modulation of hepatocyte glucose metabolism by pharmacological agents" Diabetologia, 47 Supp 1, A 214, 589 (2004).
West, Anthony R., "Solid State Chemistry and its Applications" Wiley, New York, pp. 358 and 365 (1988).
Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).
Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).
Wolff, Manfred E. "Burger's Medicinal Chemistry", 5th Edition, Part I, John Wiley & Sons, pp. 975-977 (1995).
Yakushijin et al. "Intramolecular ring formation of phenyl azide and furan moieties" Chem. Pharm. Bull. 30(1):140-151 (1982).
Yakushijin et al. "Intramolecular ring formation of phenyl azide and furan" Heterocycles 12(8):1021-1026 (1979).
Yang et al. "Hypothalamic glucose sensor: similarities to and differences from pancreatic beta-cell mechanisms" Diabetes 48(9):1763-1772 (1999).
Yoshina et al. "Studies of heterocyclic compounds. II. Synthesis of 2-furylvinyl-benzenes and studies of polarography" Yakugaku Zasshi 88(4):398-404 (1968).
Yoshina et al. "Studies of heterocyclic compounds. III. Synthesis of methyl 5-(2-phenylvinyl)2-furoate" Yakugaku Zasshi 88(4):405-409 (1968).
Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).
Yoshina et al. "Studies of heterocyclic compounds. VI. 2-(Carbomethoxy-2-furyl)vinyl benzenes and their ultraviolet spectra" Yakugaku Zasshi 88(4):977-983 (1968).
Youssefyeh et al. "Development of high-affinity 5-HT3 receptor antagonists. 1. Initial structure-activity relationship of novel benzamides" J. Med. Chem. 35(5): 895-903 (1992).
Zhang et al. "Synthesis based on affinity separation (SAS): separation of products having barbituric acid tag from untagged compounds by using hydrogen bond interaction" Synlett 5:590-596 (2001).

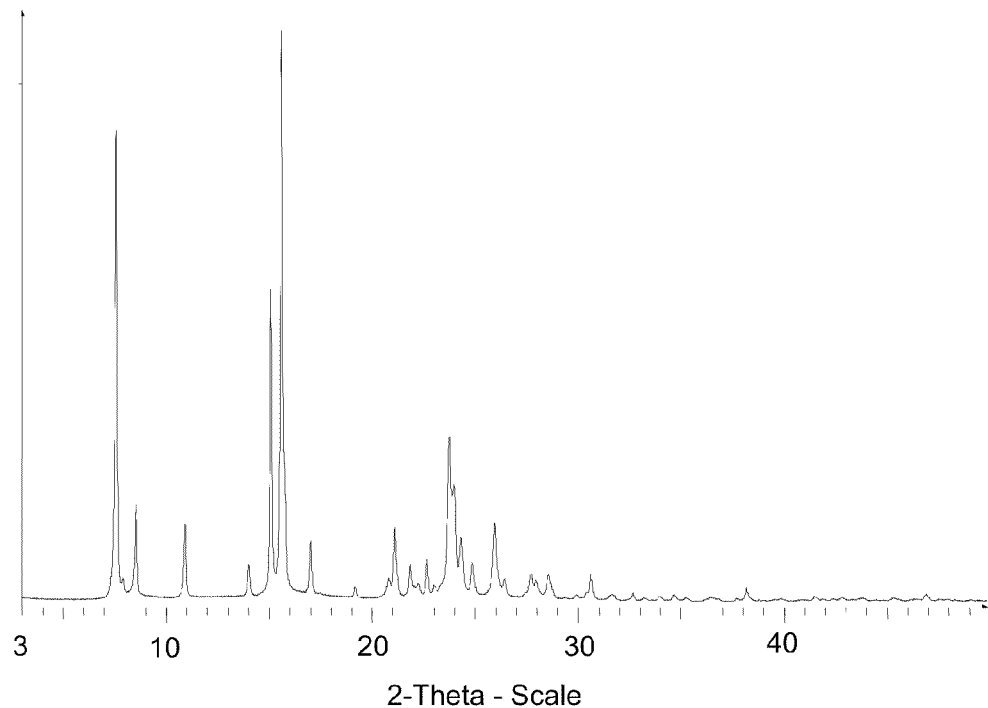
Table 1 – Form 6
| d-value (Å) | Relative Intensity | 2θ (°) |
|---|---|---|
| 11.8 | vs | 7.5 |
| 10.5 | m | 8.4 |
| 8.2 | m | 10.8 |
| 6.4 | m | 13.9 |
| 5.9 | s | 15.0 |
| 5.7 | vs | 15.5 |
| 5.2 | m | 16.9 |
| 3.75 | s | 23.7 |
| 3.44 | m | 25.9 |
Note: Relative intensities are quoted above rather than absolute intensities: vs = >80, s = 80-28, m = 28-7, w = 7-3, vw = <3
Figure 1: XRPD pattern for Form 6

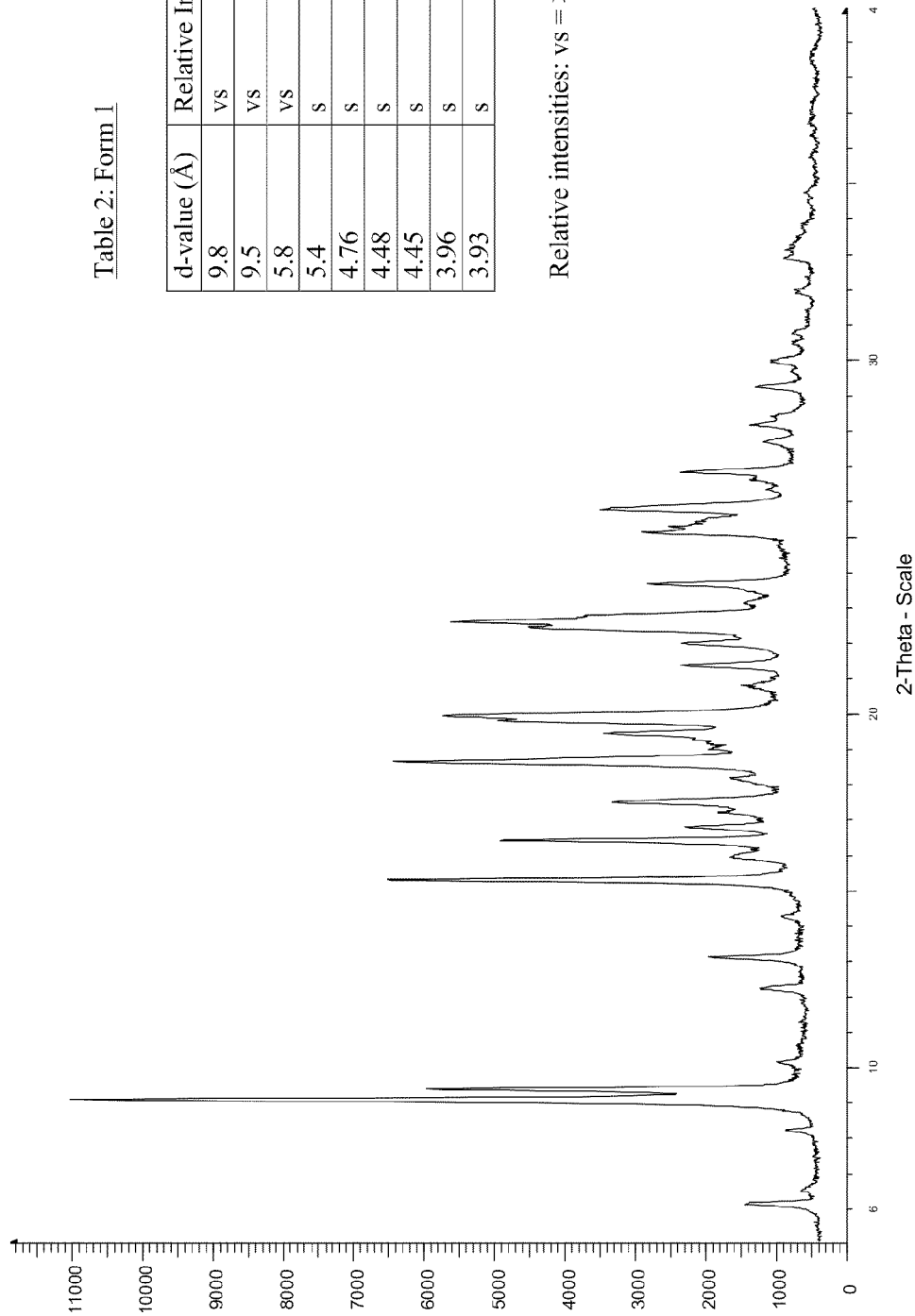
Table 2: Form 1
| d-value (Å) | Relative Intensity | 2θ (°) |
|---|---|---|
| 9.8 | vs | 9.1 |
| 9.5 | vs | 9.3 |
| 5.8 | vs | 15.3 |
| 5.4 | s | 16.4 |
| 4.76 | s | 18.6 |
| 4.48 | s | 19.8 |
| 4.45 | s | 19.9 |
| 3.96 | s | 22.4 |
| 3.93 | s | 22.6 |
Relative intensities: vs = >50, s = 30-50
Figure 2: XRPD pattern for Form 1

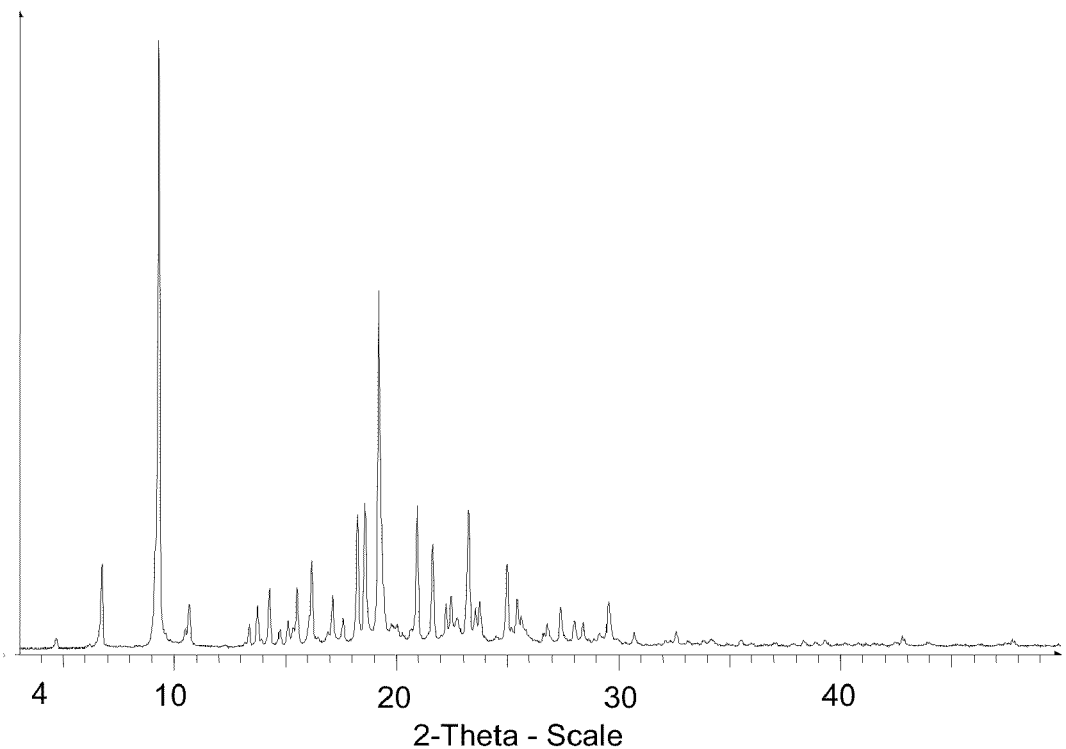
Figure 3: XRPD pattern for Form 2

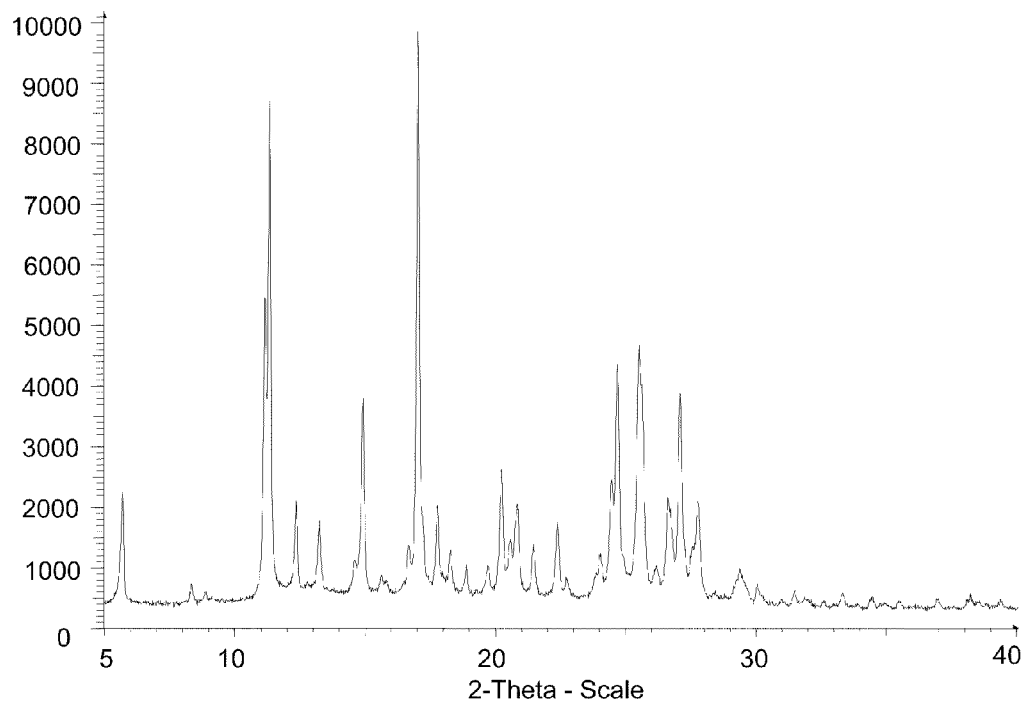
Table 3: Form 3
| d-value (Å) | Relative Intensity | 2θ (°) |
|---|---|---|
| 7.9 | vs | 11.1 |
| 7.8 | vs | 11.3 |
| 5.9 | s | 14.9 |
| 5.2 | vs | 17.0 |
| 4.39 | m | 20.2 |
| 3.64 | m | 24.4 |
| 3.60 | s | 24.7 |
| 3.49 | s | 25.5 |
| 3.29 | s | 27.1 |
Relative Intensities: vs = >50, s = 30-50 m=20-30
Figure 4: XRPD pattern for Form 3

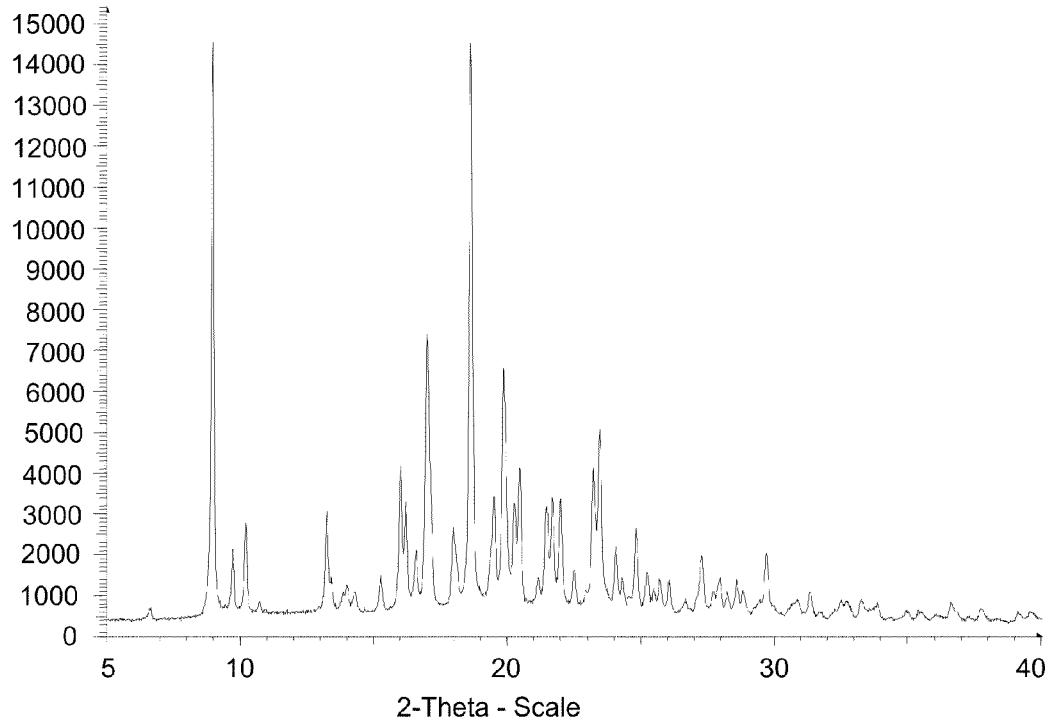
Table 4: Form 4
| d-value (Å) | Relative Intensity | 2θ (°) |
|---|---|---|
| 9.9 | vs | 9.0 |
| 5.5 | m | 16.0 |
| 5.5 | m | 16.2 |
| 5.2 | s | 17.0 |
| 4.76 | vs | 18.6 |
| 4.55 | m | 19.5 |
| 4.47 | s | 19.9 |
| 4.38 | m | 20.3 |
| 4.34 | m | 20.5 |
| 4.14 | m | 21.5 |
| 4.09 | m | 21.7 |
| 4.04 | m | 22.0 |
| 3.83 | m | 23.2 |
| 3.79 | s | 23.5 |
Relative Intensities: vs = >50, s = 30-50 m=20-30
Figure 5: XRPD pattern for Form 4

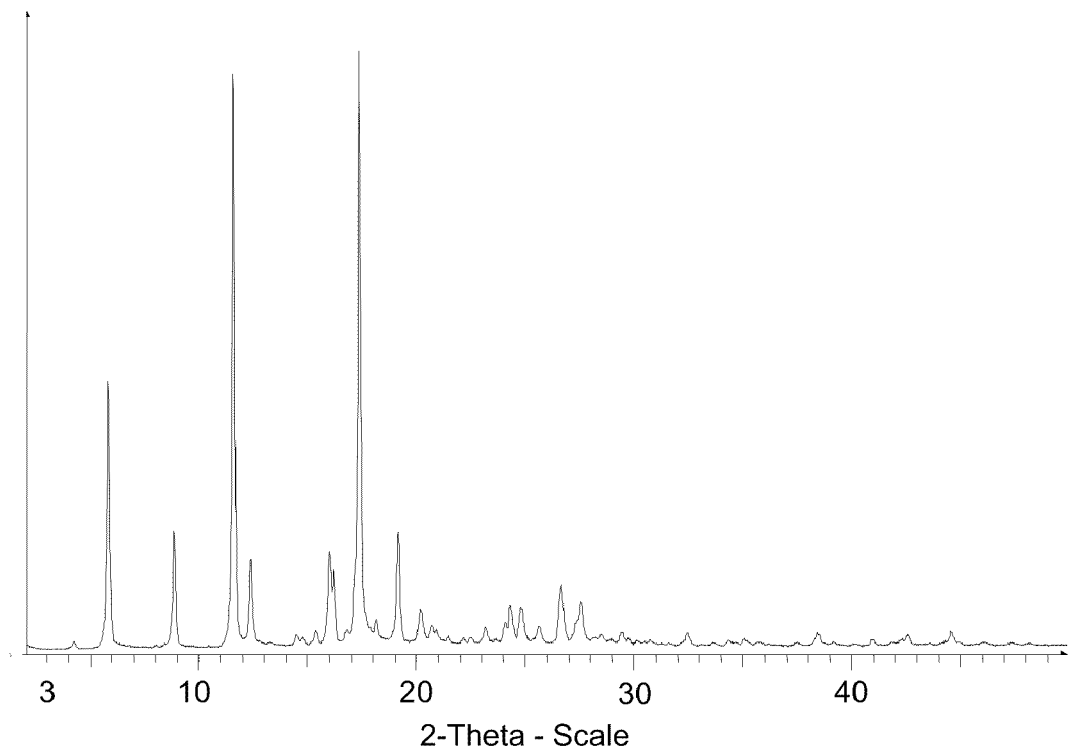
Figure 6: XRPD pattern for Form 5

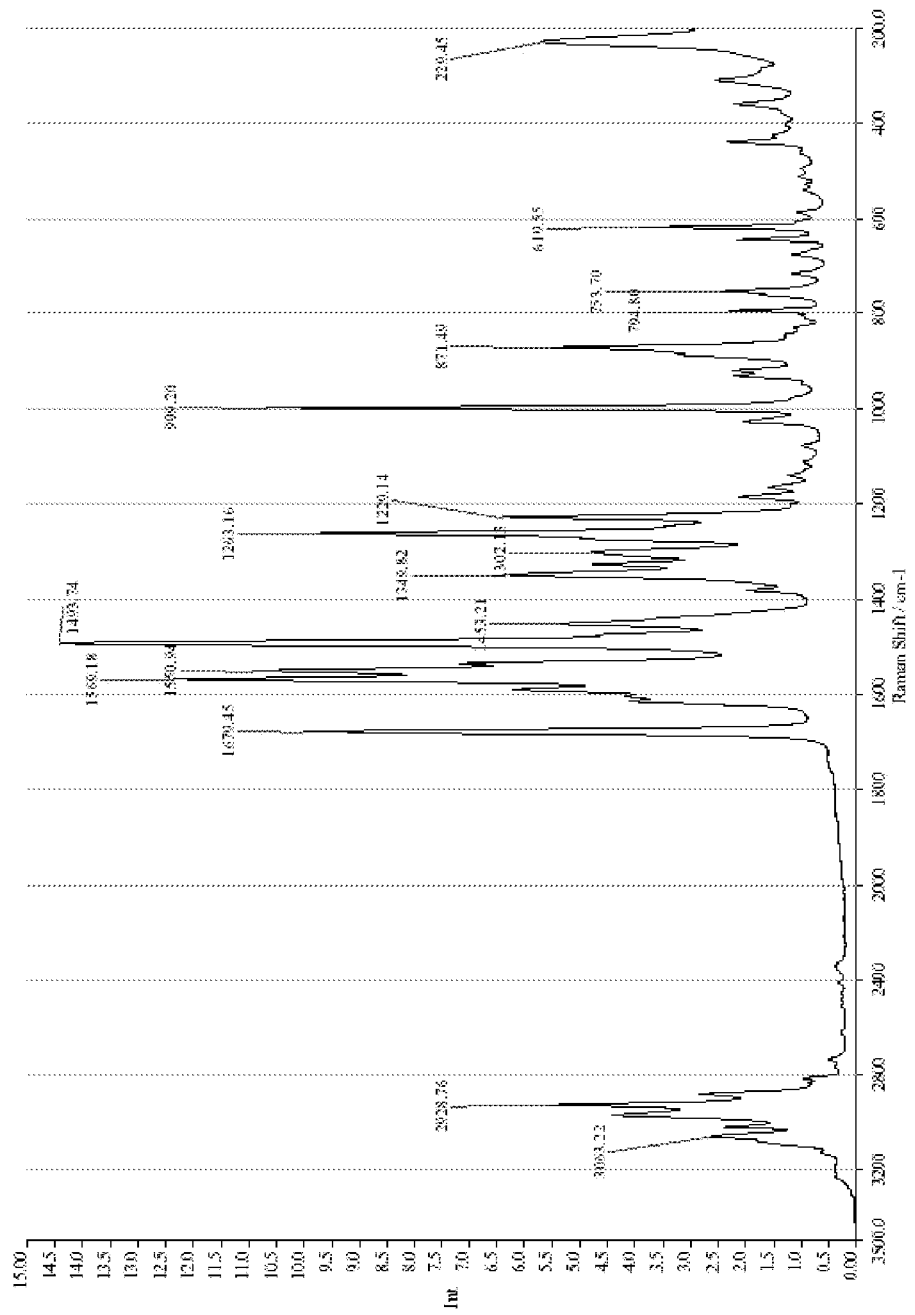
Figure 7: Raman spectrum for Form 1

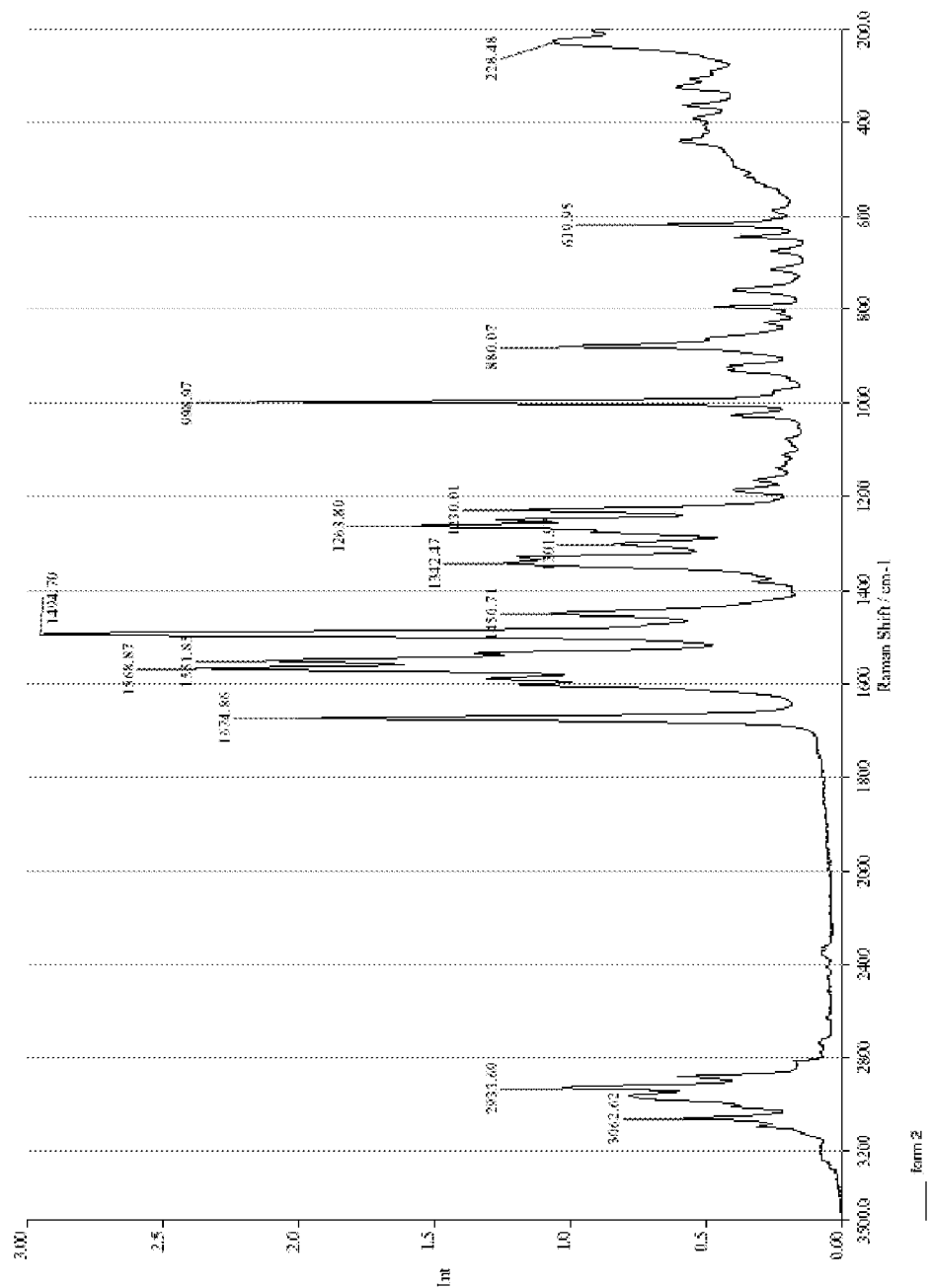

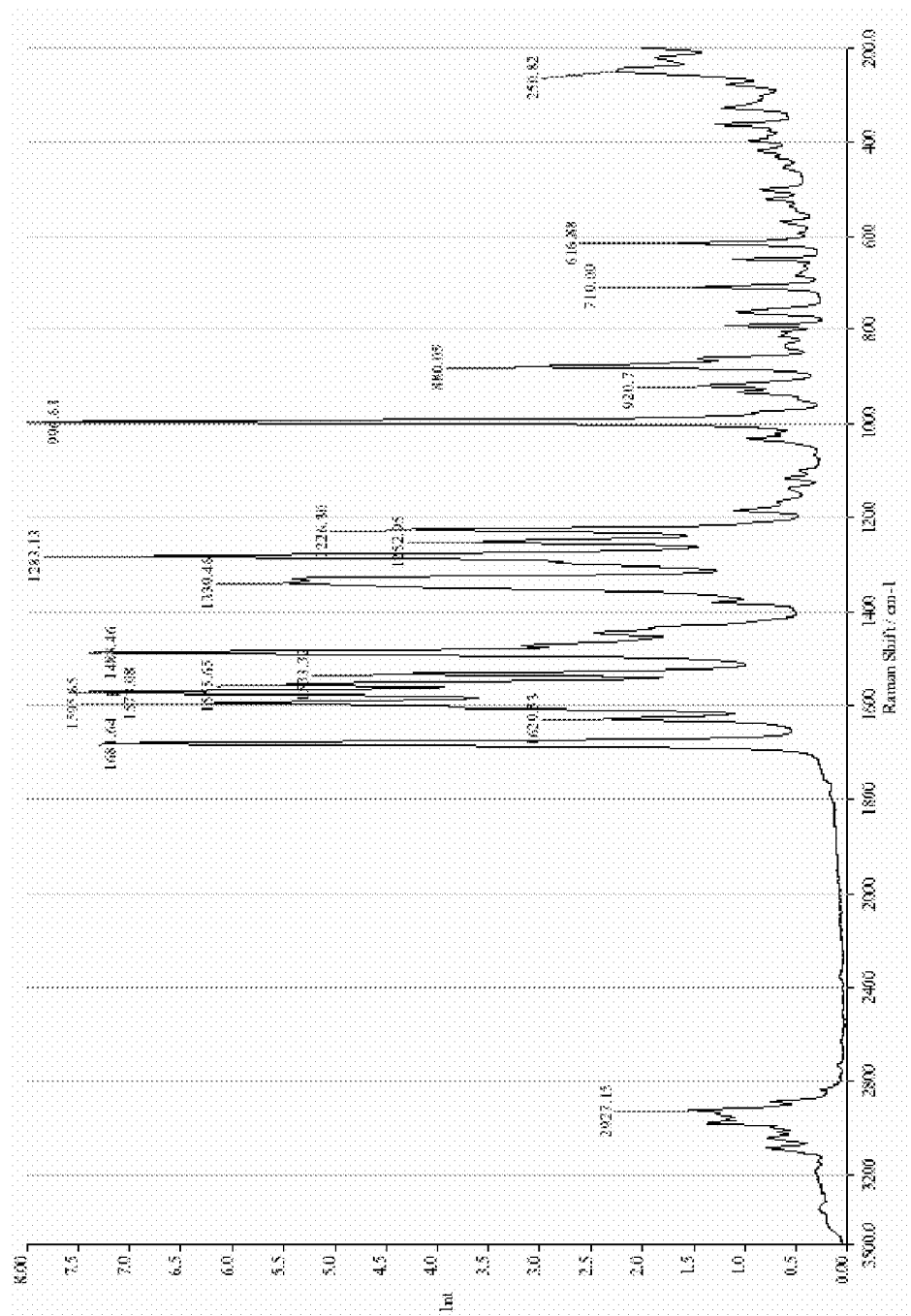
Figure 9: Raman spectrum for Form 3

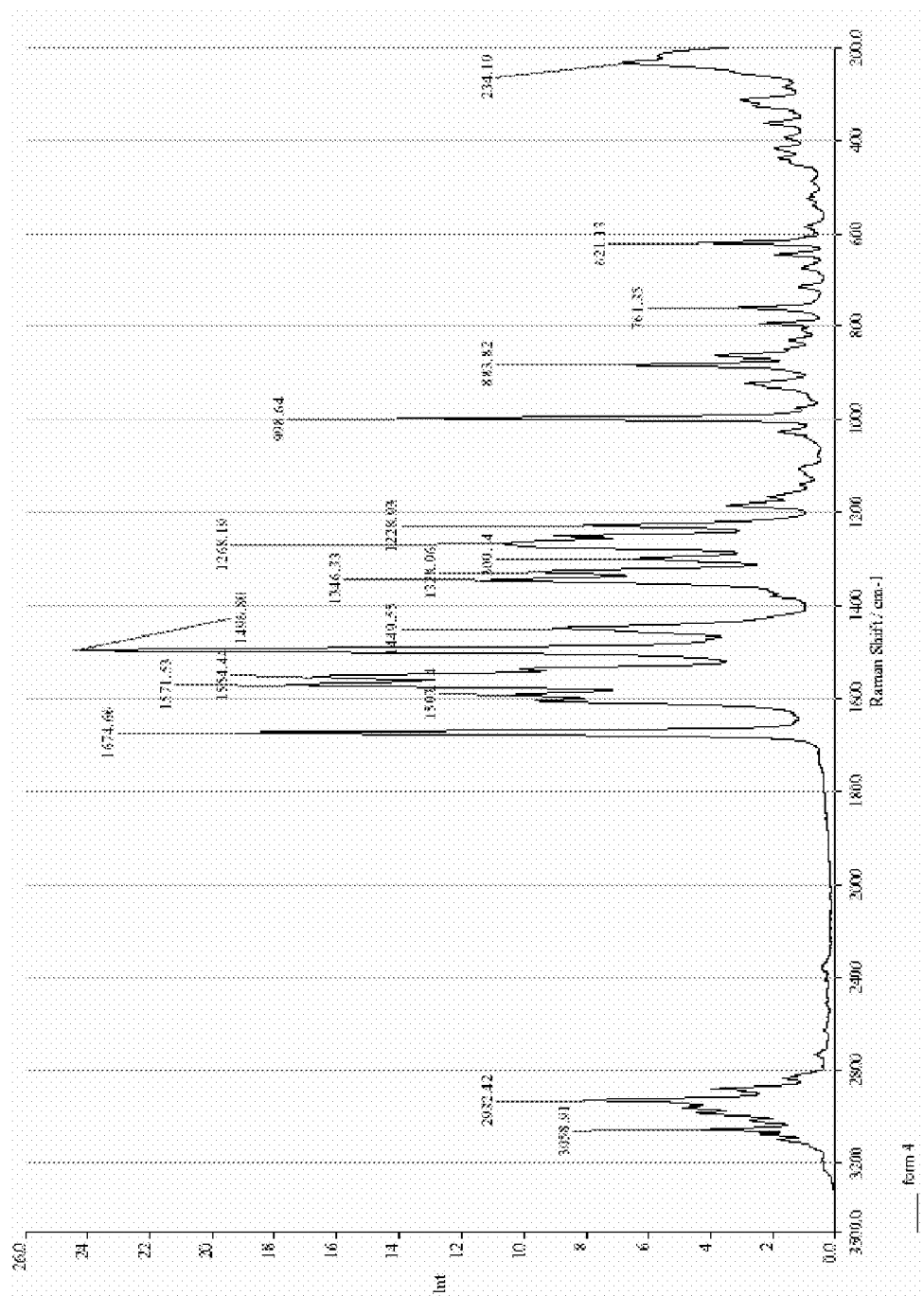
Figure 10: Raman spectrum for Form 4

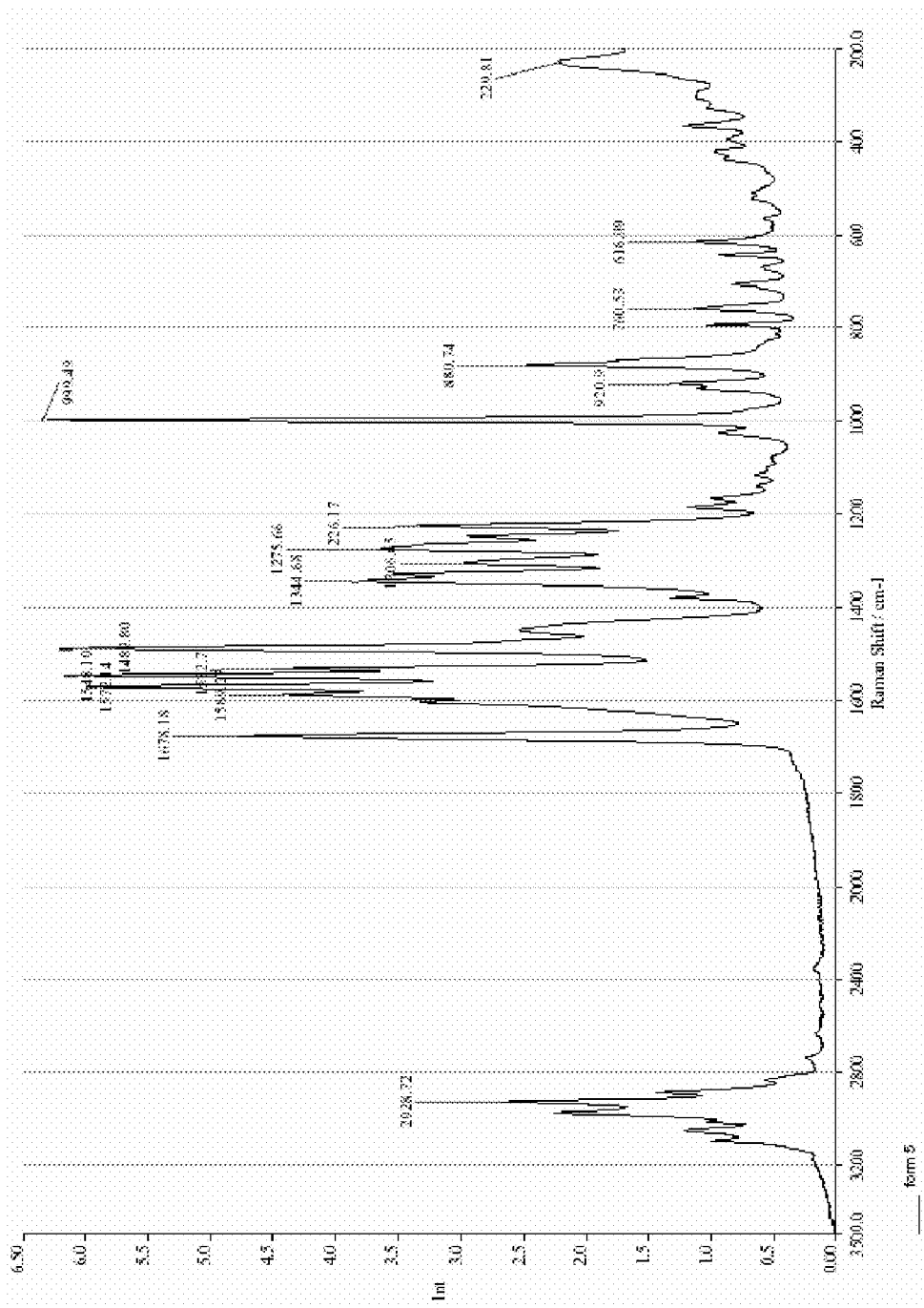
Figure 11: Raman spectrum for Form 5

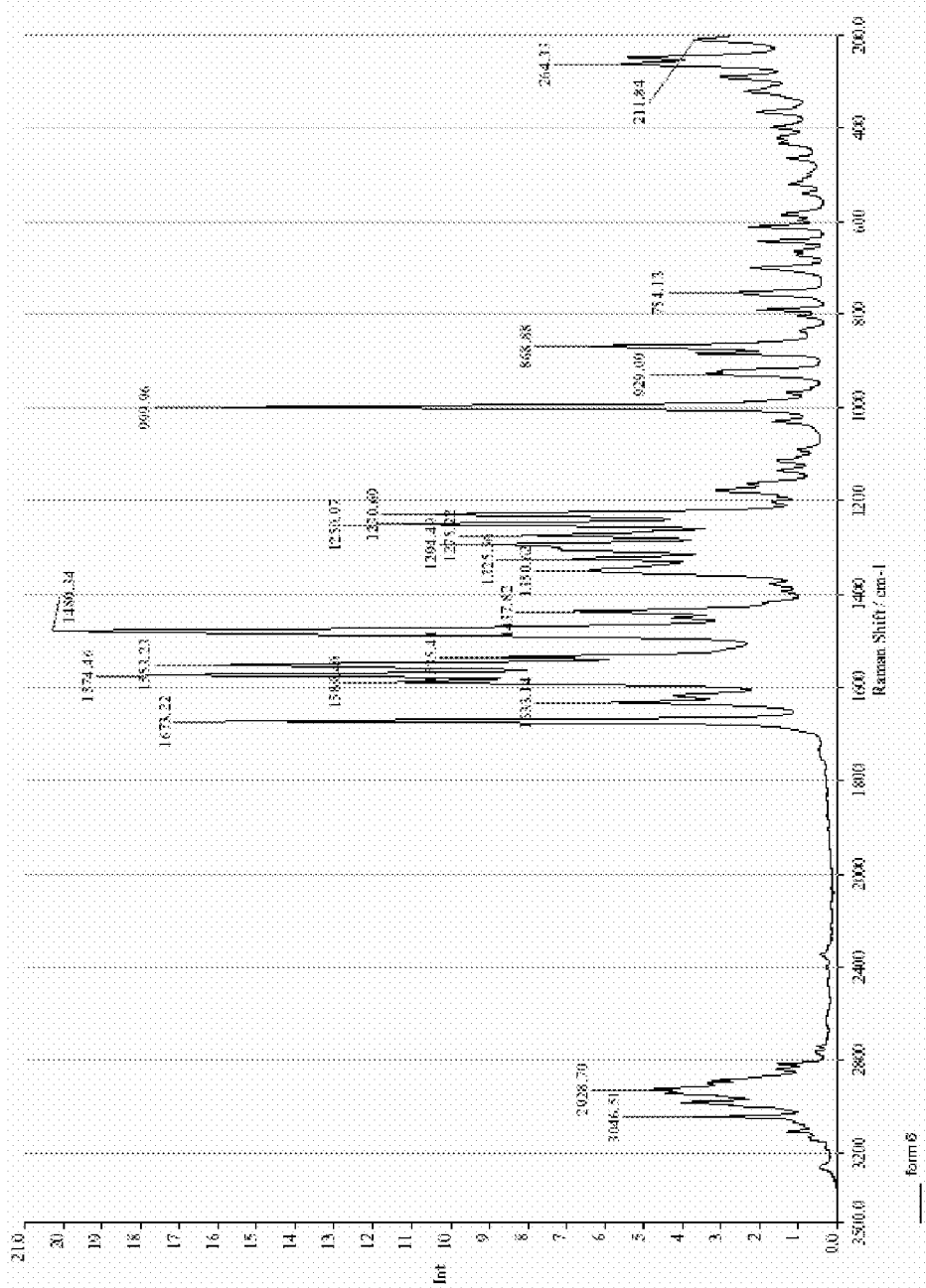
Figure 12: Raman spectrum for Form 6

CRYSTALLINE POLYMORPHIC FORM OF GLUCOKINASE ACTIVATOR

This application claims the benefit under 35 U.S.C. §119 (a-d) of Application No. 0902406.8 (GB) filed on 13 Feb. 2009.

The present invention relates to a novel crystalline form of 3-{[5-(azetidin-1-ylcarbonyl)pyrazin-2-yl]oxy}-5-{[(1S)-1-methyl-2-(methyloxy)ethyl]oxy}-N-(5-methylpyrazin-2-yl)benzamide ("the compound") illustrated in Formula (I) hereinafter, which compound is an activator of glucokinase (GLK or GK) and is useful as a pharmaceutical compound, for example in the treatment of diabetes and/or obesity. The invention also relates to processes for the manufacture of the crystalline form, pharmaceutical compositions comprising the crystalline form and the use of the crystalline form in medical treatment.

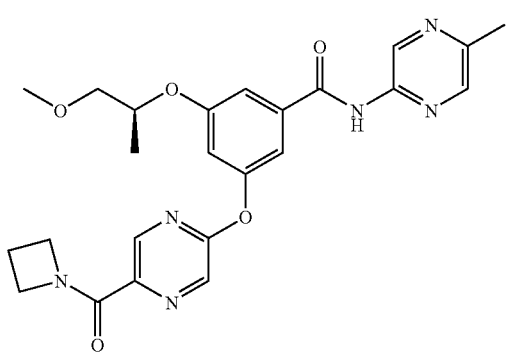

(I)

Our International Patent Application WO 2007/007041 discloses three crystalline forms of the compound. The first, Form 1 was crystallised from tert-butylmethyl ether and was found to have a melting onset point of 110.3° C. The second, Form 2, was made from a slurry of Form 1 in methanol and water, and had a melting onset point of 110.2° C. It can also be formed by crystallisation from ethyl acetate and methyl isobutyl ketone at room temperature. These two forms, although with similar melting point data, were found to have different X-Ray Powder Diffraction patterns. A third crystal form, Form 3, a dihydrate was also disclosed as the product of crystallisation by stirring a slurry of the compound in water. This form appears to be the most stable in the presence of water. XRPD patterns for all these three forms can be seen in FIGS. 2-4 respectively.

Subsequently, fourth and fifth crystal forms were found. Form 4 has been observed from several slurry experiments in ethyl acetate, methyl ethyl ketone and ethanol at 4° C. and methyl ethyl ketone and ethanol at room temperature (RT), and from crystallisation in methyl ethyl ketone at RT.

Form 5 is the form obtained when the dihydrate Form 3 is dehydrated. Re-hydration of Form 5 results in Form 3.

We have now surprisingly and unexpectedly discovered that the compound can be prepared in another, more stable crystalline form from isopropyl alcohol (IPA). This form is referred to herein as "Form 6" of the compound (of formula (I)).

According to the present invention there is provided crystalline Form 6 of the compound.

In another aspect of the invention, there is provided a crystalline form of the compound, Form 6, having an X-ray powder diffraction pattern with peaks at d-value (Å) 11.8 and 5.7.

In another aspect of the invention, there is provided a crystalline form of the compound, Form 6, having an X-ray powder diffraction pattern with peaks at d-value (Å) 11.8, 10.5, 6.4, 5.9 and 5.7.

In another aspect of the invention, there is provided a crystalline form of the compound, Form 6, having an X-ray powder diffraction pattern with peaks at d-value (Å) 11.8, 10.5, 6.4, 5.9, 5.7 and 3.75.

In another aspect of the invention, there is provided a crystalline form of the compound, Form 6, having an X-ray powder diffraction pattern with peaks at d-value (Å) 11.8, 10.5, 8.2, 6.4, 5.9, 5.7, 5.2, 3.75 and 3.44.

According to the present invention there is provided a crystalline form of the compound, Form 6, having an X-ray powder diffraction pattern with peaks at 2-theta angle (2θ)=7.5 and 15.5°.

In another aspect of the invention, there is provided a crystalline form of the compound, Form 6, having an X-ray powder diffraction pattern with peaks at 2-theta angle (2θ)=7.5, 8.4, 13.9, 15.0 and 15.5°.

In another aspect of the invention, there is provided a crystalline form of the compound, Form 6, having an X-ray powder diffraction pattern with peaks at 2-theta angle (2θ)=7.5, 8.4, 13.9, 15.0, 15.5 and 23.7°.

In another aspect of the invention, there is provided a crystalline form of the compound, Form 6, having an X-ray powder diffraction pattern with peaks at 2-theta angle (2θ)=7.5, 8.4, 10.8, 13.9, 15.0, 15.5, 16.9, 23.7 and 25.9°.

In a further aspect of the invention, there is provided a crystalline form of the compound, Form 6, having an X-ray powder diffraction pattern substantially as shown in FIG. 1.

Form 6 obtained according to the present invention is substantially free from other crystal and non-crystal forms of the compound. The term "substantially free from other crystal and non-crystal forms" shall be understood to mean that the desired crystal form contains less than 50%, preferably less than 20%, more preferably less than 10%, more preferably less than 5% of any other forms of the compound.

The X-ray powder diffraction (referred to herein as XRPD or XRD) pattern was determined by mounting a sample on a zero background holder, single silicon crystal, and spreading out the sample into a thin layer. Using a Bruker D8 Advance theta-2 theta diffractometer with a VÅNTEC-1 detector, the sample was spun (to improve counting statistics) and irradiated with X-rays generated by a copper tube operated at 30 kV and 50 mA. Automatic variable divergence slits were used.

The X-ray powder diffraction (XRPD) patterns in this were obtained in Bragg-Brentano geometry.

The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York. X-ray powder diffraction data were corrected by using corundum as an internal reference and measured with variable slits.

The X-ray powder diffraction pattern of a typical sample of Form 6 is shown in FIG. 1 hereinafter.

It will be understood that the 2-theta values of the X-ray powder diffraction pattern may vary slightly from one machine to another and also depending on variations in sample preparation and batch to batch variation, and so the values quoted are not to be construed as absolute. It will also be understood that the relative intensities of peaks may vary depending on orientation effects so that the intensities shown in the XRD trace included herein are illustrative and not intended to be used for absolute comparison.

Form 6 may also be characterised by other analytical techniques known in the art such as by Differential Scanning Calorimetry (DSC), which gave a melting point of Form 6 of 111° C.

Forms 1 to 6 may also be analysed by Raman Spectroscopy. Raman Spectra for each polymorph are shown in FIGS. 7 to 12. The wavelength shifts of specific peaks between the different forms are small hence account must be taken of the interrelationship of several peaks and the overall spectral signal to distinguish between the forms. Raman spectra were measured using a Perkin-Elmer Spectrum GX Near-IR FT-Raman spectrometer according to standard procedures. The laser power was set to 500 mW and the resolution to 4 cm$^{-1}$. The accuracy of the wavelength calibration was ±1 cm$^{-1}$. Substance was filled in NMR tubes and placed in a sample holder rotating the tube during measurement to avoid sample heating. The spectra were not corrected for instrumental response.

Form 6 may be made by slurrying a mixture of forms 1 and 4, such as approximately a 1:1 mixture, in iso-propyl alcohol (IPA) at elevated temperatures over a prolonged period. Suitably, the slurry is maintained at 35-50° C. for 8-15 days. It will be appreciated that at higher temperatures, less time is required to achieve conversion into Form 6; thus Form 6 may be obtainable at less than 35° C. after a more extended period. Suitably the concentration of the slurry is approximately 30 mg of the compound as a mixture of Forms 1 and 4, in 50-300 μl of IPA.

Form 6 may also be made from a solution of the compound of formula (I) in a number of solvents by seeding with a small amount of Form 6. Suitably, the solution is made from Form 1 of the compound of formula (I) dissolved in, for example, butyronitrile, 2-methyltetrahydrofuran optionally mixed with heptane, n-butyl acetate, acetonitrile, methylisobutylketone optionally mixed with heptane, ethyl acetate or isopropanol. In particular, butyronitrile and methylisobutylketone optionally mixed with heptane are suitable. Alternatively ethyl acetate or isopropanol may be used as the solvent. Seeding is generally carried out at elevated temperatures, for example 45° C., though it will be appreciated that the precise temperature may be dependent on the physical properties of the solvent used. It will be appreciated that it may be possible to obtain Form 6 by a similar seeding process to that above from solutions of other Forms than Form 1.

For example, Form 6 may be obtained by seeding a solution of the compound in butyronitrile at 45° C., holding at this temperature for example for 3 hours, cooling slowly to 15° C. and then maintaining the mixture at this temperature for a prolonged period such as at least 24 hours. Further details of suitable conditions may be found in the accompanying examples.

Alternatively, Form 6 may be obtained by seeding a solution of the compound in methyl isobutyl ketone at 45° C., holding at this temperature for 6 hours, then reducing the temperature stepwise, holding the mixture at each of the following temperatures for 6 hours: 40° C., 35° C., 30° C., 20° C.; then reducing the temperature to 10° C. for 3 hours and optionally adding n-heptane at this temperature. Alternatively, Form 6 may be obtained by seeding a solution of the compound in methyl isobutyl ketone at 45° C., holding at this temperature for 6 hours, then reducing the temperature stepwise, 40° C. 6 hrs, 30° C. 6 hrs then 0° C. Further details of suitable conditions may be found in the accompanying examples.

Therefore in another aspect of the invention, there is provided a process for making Form 6 of 3-{[5-(azetidin-1-ylcarbonyl)pyrazin-2-yl]oxy}-5-{[(1S)-1-methyl-2-(methyloxy)ethyl]oxy}-N-(5-methylpyrazin-2-yl)benzamide, comprising:

a) suspending a mixture of Form 1 and 4 of 3-{[5-(azetidin-1-ylcarbonyl)pyrazin-2-yl]oxy}-5-{[(1S)-1-methyl-2-(methyloxy)ethyl]oxy}-N-(5-methylpyrazin-2-yl)benzamide in IPA at 35-50° C. for a prolonged period (for example 8-15 days); or b) forming a suspension of Form 1 in IPA at 35° C., then seeding with a small amount of Form 6 after 1 hour and leaving the mixture for a prolonged period (such as 2 days); or c) forming a solution of Form 1 in butyronitrile at 45° C. then seeding with a small amount of Form 6, after at least 3 hours cooling slowly to 15° C. and leaving the mixture for a prolonged period at this temperature (such as 24 h); or d) forming a solution of Form 1 in butyronitrile at 45° C. then seeding with a small amount of Form 6, after at least 6 hours cooling stepwise in 5, 5, 5, 10 and 10° steps to 10° C. holding the mixture for several hours at each step, then optionally adding heptane at 10° C. and holding the mixture for a further period.

Alternatively solutions are formed in either ethyl acetate or isopropanol followed by seeding and cooling, optionally stepped cooling.

The utility of the compound of the invention may be demonstrated by standard tests and clinical studies, including those described in WO 2007/007041.

According to a further feature of the invention is a method of treating a disease condition wherein activation of glucokinase is beneficial which comprises administering to a warm-blooded mammal an effective amount of Form 6 of the compound. The invention also relates to the use of Form 6 in the manufacture of a medicament for use in a disease condition. Suitable disease conditions include diabetes and/or obesity.

In a further aspect of the invention there is provided a compound of formula (I) in Form 6 as hereinbefore defined, for use as a medicament. In a further aspect of the invention there is provided a compound of formula (I) in Form 6 as hereinbefore defined, for use as a medicament for the treatment of a disease mediated through glucokinase, in particular type II diabetes and/or obesity.

The compound of the invention may be administered to a warm-blooded animal, particularly a human, in need thereof for treatment of a disease in which glucokinase is implicated, in the form of a conventional pharmaceutical composition. Therefore in another aspect of the invention, there is provided a pharmaceutical composition comprising Form 6 in admixture with a pharmaceutically acceptable diluent or carrier.

Such compositions may be administered in standard manner for the disease condition that it is desired to treat, for example by oral, topical, parenteral, buccal, nasal, vaginal or rectal administration or by inhalation. For these purposes the compound may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solution or suspensions or sterile emulsions. In the above examples of formulations, for those wherein polymorphic form may be retained (ie non-solution formulations), then the invention comprises those formulations wherein Form 6 is substantially retained within the formulation, and wherein there is not substantial (such as >50%) conversion in polymorphic form. A preferred route of administration is oral. The compound will be administered to humans at a daily dose in, for example, the ranges set out in WO 2007/007041. The daily doses may be given in divided doses as necessary, the precise amount of the compound received and the route of administration depending on the weight, age and sex of the patient being treated and on the particular disease condition being treated according to principles known in the art.

Suitable pharmaceutically acceptable excipients for a tablet formulation include, for example, one or more inert diluents (which may also be termed "fillers") such as lactose, sucrose, glucose, mannitol, sorbitol, microcrystalline cellulose, silicified microcrystalline cellulose, sodium carbonate, monobasic calcium phosphate, dibasic calcium phosphate (including dibasic calcium phosphate dihydrate and dibasic calcium phosphate anhydrate), tribasic calcium phosphate, calcium carbonate and the like;

one or more disintegrants such as starch (such as potato, maize or corn), sodium starch glycolate, sodium carboxymethyl cellulose (NaCMC), low substituted hydroxypropyl cellulose (L-HPC), crosslinked polyvinyl pyrrolidone, algenic acid and the like;

one or more binders such as starch (such as potato, maize or corn), polyvinyl pyrrolidone, microcrystalline cellulose, a polyethylene glycol (PEG), a polyethylene oxide (PEO), a hydroxypropylmethyl cellulose (HPMC) of a low molecular weight, a methyl cellulose (MC) of a low molecular weight, a hydroxypropyl cellulose (HPC) of a low molecular weight, a hydroxyethyl cellulose (HEC) of a low molecular weight, a sodium carboxymethyl cellulose of a low molecular weight and the like;

one or more lubricants such as magnesium stearate, stearic acid, calcium stearate, stearyl alcohol, sodium stearyl fumarate;

a glidant such as talc or a colloidal silica;
a surfactant such as, for example sodium lauryl sulphate;
a colourant, a flavouring, a preservative;
and anti-oxidants.

Tablet formulations may be uncoated or coated using conventional coating agents and procedures well known in the art. It will be appreciated that some of the above mentioned excipients which may be present in a final oral (for example tablet) composition of the invention may have more than one of the above stated functions. Tablet formulations comprising Form 6 may, for example, be manufactured with the following strengths: 1 mg, 2.5 mg, 5 mg, 10 mg, 20 mg, 25 mg, 45 mg, 50 mg, 75 mg, 100 mg, 150 mg, 200 mg, 250 mg and 500 mg.

In one aspect of the invention there is provided a tablet formulation (wherein %=% by weight of total tablet weight) comprising:
Form 6: 1 to 30%, such as 10 to 25%, for example 12.5%;
Filler: 50 to 95%, such as 45-90% of mannitol plus 2 to 20% microcrystalline cellulose, for example 75% mannitol plus 4% microcrystalline cellulose;
Disintegrant: 3 to 15%, such as 3 to 10%, for example 5% low substituted hydroxypropyl cellulose;
Lubricant: 1 to 5% such as 1 to 3%, for example 2.3% magnesium stearate;
surfactant: 0.1 to 3%, such as 0.75 to 1.25%, for example 1% sodium lauryl sulphate.

In one aspect of the invention there is provided a tablet formulation (wherein %=% by weight of total tablet weight) comprising:
Form 6: 1 to 30%, such as 12 to 18%, for example 15%;
Filler: 70 to 92%, such as 50-90% of mannitol plus 2 to 20% microcrystalline cellulose, for example 73.4% mannitol plus 3.86% microcrystalline cellulose;
Disintegrant: 3 to 10%, such as 3 to 7%, for example 5% sodium starch glycolate;
Lubricant: 1 to 5% such as 1 to 2%, for example 1.75% magnesium stearate;
surfactant: 0.1 to 3%, such as 0.75 to 1.25%, for example 1% sodium lauryl sulphate.

In one aspect of the invention there is provided a tablet formulation (wherein %=% by weight of total tablet weight of uncoated tablets) comprising:
Form 6: 1 to 30%, such as 10-25%, for example 20%;
Filler: 50 to 95%, such as 45-90% of mannitol plus 2 to 20% microcrystalline cellulose, for example 67.9% mannitol plus 3.6% microcrystalline cellulose;
Disintegrant: 3 to 10%, such as 3 to 8%, for example 5% sodium starch glycolate;
Lubricant: 1 to 5% such as 1 to 3%, for example 2.5% magnesium stearate;
surfactant: 0.1 to 3%, such as 0.75 to 1.25%, for example 1% sodium lauryl sulphate.

In one aspect of the invention there is provided a tablet formulation (wherein %=% by weight of total tablet weight of uncoated tablets) comprising:
Form 6: 1 to 30%, such as 10-25%, for example 20%;
Filler: 50 to 95%, such as 45 to 90% of mannitol plus 2 to 20% microcrystalline cellulose, for example 68% mannitol plus 3.6% microcrystalline cellulose;
Disintegrant: 3 to 10%, such as 3 to 8%, for example 5% sodium carboxymethyl cellulose;
Lubricant: 1 to 5% such as 1 to 3%, for example 2.5% magnesium stearate;
surfactant: 0.1 to 3%, such as 0.75 to 1.25%, for example 1% sodium lauryl sulphate.

In one aspect of the invention there is provided a tablet formulation (wherein %=% by weight of total tablet weight of uncoated tablets) comprising:
Form 6: 1 to 30%, such as 10-25%, for example 20%;
Filler: 50 to 95%, such as 45 to 90% of mannitol plus 2 to 20% microcrystalline cellulose, for example 65% mannitol plus 3.4% microcrystalline cellulose;
Disintegrant: 3 to 15%, such as 3 to 10%, for example 8% low substituted hydroxypropyl cellulose;
Lubricant: 1 to 5% such as 1 to 3%, for example 2.5% magnesium stearate;
surfactant: 0.1 to 3%, such as 0.75 to 1.25%, for example 1% sodium lauryl sulphate.

In one aspect of the invention there is provided a tablet formulation comprising Form 6, mannitol, microcrystalline cellulose, sodium starch glycolate, magnesium stearate and sodium lauryl sulfate.

In one aspect of the invention there is provided a tablet formulation comprising Form 6, mannitol, microcrystalline cellulose, sodium carboxymethyl cellulose, magnesium stearate and sodium lauryl sulfate.

In one aspect of the invention there is provided a tablet formulation comprising Form 6, mannitol, microcrystalline cellulose, low substituted hydroxypropyl cellulose, magnesium stearate and sodium lauryl sulfate.

Tablets may be made by conventional means, including direct compression of the powder blend and compaction of granules obtained by wet granulation in a convective mixer or in a fluidised bed equipment or by dry granulation, such as, for example, roller compaction. A dry process, such as dry granulation, is likely to minimise any possible interchange of polymorphic form during the formulation process.

Compositions for oral use may further be in the form of capsules in which the active ingredient is mixed with one or more inert diluent(s), as previously described.

According to a further feature of the invention, there is provided a process for the manufacture of a pharmaceutical composition containing Form 6 as active ingredient, which comprises admixing Form 6 together with a pharmaceutically acceptable carrier.

In one aspect of the invention there is provided a process for the manufacture of a pharmaceutical composition containing Form 6 as active ingredient, which comprises;
a first blending step, in which Form 6 is mixed with one or more filler(s), disintegrant(s) and surfactant(s) in a diffusion mixer,
a second blending step, in which a lubricant is added to the powder blend and the material is mixed in a diffusion mixer, dry granulation of the material by roller compaction,
final mixing, in which the granules are mixed with a lubricant in a diffusion mixer and tabletting by compaction of the granules.

In one aspect of the invention there is provided a process for the manufacture of a is pharmaceutical composition containing Form 6 as active ingredient, which comprises;
admixing Form 6 with one or more filler(s) and disintegrant(s) in a high-shear mixer, wet granulation of the powder blend in a high-shear mixer,
drying of the wet mass,
milling of the granules,
final mixing, in which the granules are mixed with a lubricant in a diffusion mixer, and tabletting by compaction of the granules.

In one aspect of the invention there is provided a process for the manufacture of a pharmaceutical composition containing Form 6 as active ingredient, which comprises;
wet milling of Form 6 in water with a binder, such as, for example HPMC, to produce a suspension of Form 6 in water having a size distribution that makes it suitable for spray layering onto cores, such as, for example, microcrystalline cellulose cores,
spray layering of a suspension of Form 6 in water onto cores, such as, for example, microcrystalline cellulose cores, in a fluidised bed equipment to produce immediate release pellets,
mixing the pellets with one or more filler(s) and disintegrant(s) in a diffusion mixer to produce a pellet/powder blend,
adding a lubricant to the pellet/powder blend and mixing in a diffusion mixer, and tabletting by compaction of the pellet/powder blend in a tablet press.

In one aspect of the invention there is provided a tablet formulation comprising Form 6, mannitol, microcrystalline cellulose, sodium starch glycolate, magnesium stearate and sodium lauryl sulfate.

According to a further feature of the invention, there is provided a process for the manufacture of a pharmaceutical composition containing Form 6 as active ingredient, which comprises admixing Form 6 together with a pharmaceutically acceptable carrier.

Form 6 as described herein may be applied as a sole therapy or in combination with one or more other substances and/or treatments for the indication being treated. In another aspect the invention provides a pharmaceutical combination comprising Form 6 of a compound of Formula (I) and another pharmacologically active substance particularly wherein the other pharmacologically active substance is a medicament for the treatment of type 2 diabetes or obesity or a related condition.

Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:
1) Insulin and insulin analogues;
2) Insulin secretagogues including prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-obesity agents (for example sibutramine and orlistat);
10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β blockers (eg atenolol, inderal); ACE inhibitors (eg lisinopril); Calcium antagonists (e.g. nifedipine); Angiotensin receptor antagonists (eg candesartan), α antagonists and diuretic agents (e.g. furosemide, benzthiazide);
12) Haemostasis modulators such as, antithrombotics, activators of fibrinolysis and antiplatelet agents; thrombin antagonists; factor Xa inhibitors; factor VIIa inhibitors); antiplatelet agents (e.g. aspirin, clopidogrel); anti-coagulants (heparin and Low molecular weight analogues, hirudin) and warfarin;
13) Agents which antagonise the actions of glucagon; and
14) Anti-inflammatory agents, such as non-steroidal anti-inflammatory drugs (e.g. aspirin) and steroidal anti-inflammatory agents (e.g. cortisone).

In one aspect of the invention, there is provided a combination of Form 6 of Compound (I) with metformin.

In a further aspect of the invention there is provided a combination of Form 6 of Compound (I) with insulin.

The invention will now be particularly described by way of the following examples in which the following abbreviations may be used:
vols volume equivalents
eq equivalents
w/w weight for weight
v/v volume for volume
DMSO dimethylsulfoxide
Ts tosylate (p-methylbenzenesulfonate)
TLC thin layer chromatography
NMR nuclear magnetic resonance spectroscopy
MTBE methyl tert-butyl ether
In the following non-limiting Examples, unless otherwise stated:
(i) operations were carried out at room temperature, that is in the range 18-25° C. and under an atmosphere of an inert gas such as argon or nitrogen;

(ii) yields are given for illustration only and are not necessarily the maximum attainable;

(iii) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; sextet (iv) purity of intermediates was assessed by NMR analysis;

BRIEF DESCRIPTION OF DRAWINGS

FIG. 1 shows the X-ray powder diffraction pattern for Form 6.
FIG. 2 shows the X-ray powder diffraction pattern for Form 1.
FIG. 3 shows the X-ray powder diffraction pattern for Form 2.
FIG. 4 shows the X-ray powder diffraction pattern for Form 3.
FIG. 5 shows the X-ray powder diffraction pattern for Form 4.
FIG. 6 shows the X-ray powder diffraction pattern for Form 5.
FIG. 7 shows the Raman spectrum for Form 1.
FIG. 8 shows the Raman spectrum for Form 2.
FIG. 9 shows the Raman spectrum for Form 3.
FIG. 10 shows the Raman spectrum for Form 4.
FIG. 11 shows the Raman spectrum for Form 5.
FIG. 12 shows the Raman spectrum for Form 6.

EXAMPLE 1

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide

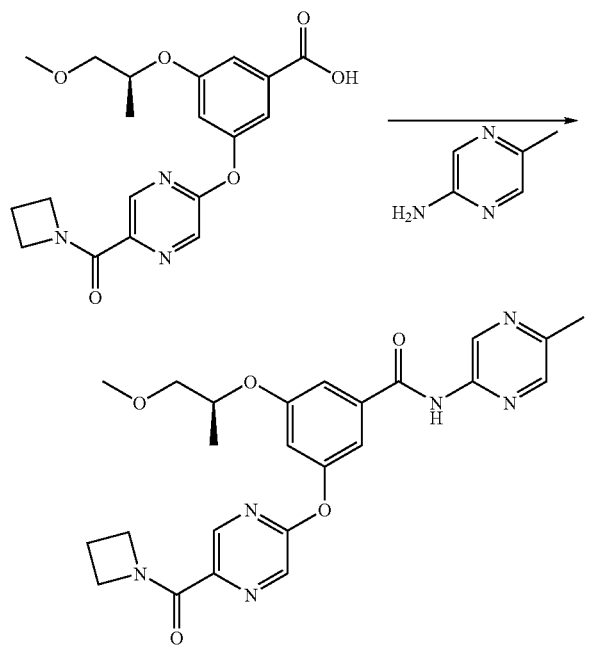

To a flask was added 3-{[5-(azetidin-1-ylcarbonyl)pyrazin-2-yl]oxy}-5-[(1S)-2-methoxy-1-methylethoxy]benzoic acid (1.0 eq), 5-methylpyrazin-2-amine (1.0 eq) and 2-methyltetrahydrofuran (3.5 vols) under a nitrogen atmosphere. The mixture was cooled to 0° C. N-methylmorpholine (5.0 eq) was added at 0° C., then 2,4,6-tripropyl-1,3,5,2,4,6-trioxatriphosphinane 2,4,6-trioxide (supplied as 50% w/w in ethyl acetate) (2.5 eq) was added in one portion via addition funnel over 45 minutes maintaining the reaction temperature at 0-5° C. The addition funnel was washed with 2-methyltetrahydrofuran (0.5 vols), then the reaction mixture was boiled under reflux under nitrogen for at least 14 hours, before being cooled to 22° C. Water (4.0 vols) was added to the reaction mixture in one portion, followed by 2-methyltetrahydrofuran (4.0 vols). After agitating for 30 minutes, the layers were separated. The upper organic layer was retained and the aqueous layer returned to the flask. 2-Methyltetrahydrofuran (4.0 vols) was added to the flask, the mixture was agitated for 30 minutes, then the layers were separated. The organic layers were combined in the flask and further 2-methyltetrahydrofuran (6.0 vols) was then added. The mixture was agitated, and 1.0N hydrochloric acid (4.0 vols) was then added. The mixture was agitated for at least 30 minutes at 22±5° C., and the layers were then separated. 1.0N Hydrochloric acid (4.0 vols) was added to the organic layer. The mixture was agitated for at least 30 minutes at 22±5° C. the mixture was separated 5% w/w Sodium hydrogen carbonate (4.0 vols) solution was added the organic layer. The mixture was agitated for at least 30 minutes at 22±5° C. then the mixture was separated. This process was repeated. Water (4.0 vols) was added to the organic layer, the mixture was agitated for at least 30 minutes at 22±5° C. then the layers were separated. The organic layer was distilled under vacuum at 35° C. collecting 19 vols of distillates. 2-Methyltetrahydrofuran (4 vols) was added, and the distillation was continued under vacuum at 35° C. collecting 6 vols distillates. Further 2-methyltetrahydrofuran (4 vols) was added and the reaction mixture sampled for water content. Further 2-methyltetrahydrofuran (4 vols) was added, and the reaction mixture was filtered through a CUNO™ filter then distilled until the pot volume was approximately 7 vols, then methyl iso-butylketone (11 vols) was added and the mixture vacuum distilled at 35° C. to a pot volume of approximately 7 vols. Methyl iso-butylketone (11 vols) was added and the mixture vacuum distilled at 35° C. to a pot volume of approximately 6 vols. N-Heptane (0.5 vols) was added to the mixture, and the temperature adjusted to 60° C., the mixture was cooled to 46° C., seeded, then cooled to 22° C. and agitated for at least 12 hours. The mixture was filtered. The solid was washed with a mixture of methyl iso-butylketone (1.5 vols)/heptane (0.16 vols). The solid was washed with heptane (~1.5 vols). The isolated solid was dried at 22° C. under vacuum to afford the title compound as an off white solid. Corrected yield was 62%. $^1$H NMR δ (400 MHz DMSO) 11.04 (s, 1H), 9.26 (s, 1H), 8.68 (s, 1H), 8.57 (s, 1H), 8.36 (s, 1H), 7.57 (bs, 1H), 7.47 (bs, 1H), 7.13 (bs, 1H), 4.81-4.77 (m, 1H), 4.58-4.54 (t, 2H), 4.11-4.07 (t, 2H), 3.55-3.47 (m, 2H), 3.3 (s, 3H), 2.48 (s, 3H), 2.34-2.26 (m, 2H), 1.26-1.25 (d, 3H)

Preparation of 3-{[5-(azetidin-1-ylcarbonyl)pyrazin-2-yl]oxy}-5-[(1S)-2-methoxy-1-methylethoxy]benzoic acid

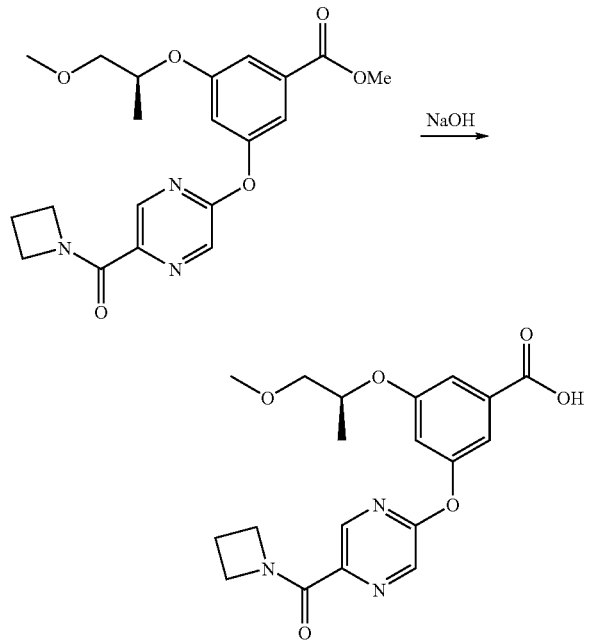

To a flask was added methyl 3-{[5-(azetidin-1-ylcarbonyl)pyrazin-2-yl]oxy}-5-[(1S)-2-methoxy-1-methylethoxy]benzoate (1.0 eq) and N-methylpyrrolidinone (7.6 vols). The contents of the flask were cooled to 10° C. Water (3.9 vols) was added, and the mixture then cooled to approximately −15° C. Sodium hydroxide (1.5 eq) was dissolved in water (2.3 vols), and the sodium hydroxide solution added slowly to the flask over one hour, maintaining the reaction temperature below −10° C. The sodium hydroxide was line washed with water (0.5 vols). The reaction mixture was held for approximately 4 hours. Acetic acid (1.25 eq) was added to the mixture at −10° C. The mixture was allowed to warm to 5° C. Acetic acid (2.37 eq) was added to the mixture, the acetic acid line washed with water (3.5 vols) and the mixture allowed to warm to 22° C. The mixture was seeded, then water (5 vols) was added to the mixture. 2N hydrochloric acid (1.5 eq) was added to the mixture until pH4 was reached. The reaction mixture was stirred for at least 14 hours, then cooled to 10° C., stirred for 1 hour at 10° C. The mixture was filtered. The solid was slurry washed with water (3×2.5 vol). The isolated solid was dried at 25° C. under vacuum to afford the title compound as an off white solid.

The solid was charged to a flask, followed by ethyl acetate (27.2 vols), and the mixture heated to reflux for at least 30 minutes. The mixture was filtered hot and approximately 13 vols removed by vacuum distillation. The mixture was cooled to 15° C., and agitated overnight at this temperature. The mixture was filtered, and the (solid) washed with ethyl acetate (2.25 vols). The isolated solid was dried at 25° C. under vacuum to afford the title compound as an off white solid. The corrected yield was 78%.

¹H NMR δ (400 MHz DMSO): 8.66 (s, 1H), 8.55 (s, 1H), 7.36 (s, 1H), 7.31 (s, 1H), 7.16 (s, 1H), 4.71-4.65 (m, 1H), 4.58-4.54 (t, 2H), 4.11-4.07 (t, 2H), 3.52-3.41 (m, 2H), 3.29 (s, 3H), 2.33-2.26 (m, 2H), 1.24-1.2 (d, 3).

Preparation of methyl (3-{[5-azetidinyl-1-ylcarbonyl)pyrazin-2-yl]oxy}-5-{[1S)-1-methyl-2-(methyloxy)ethyl]oxy})benzoate

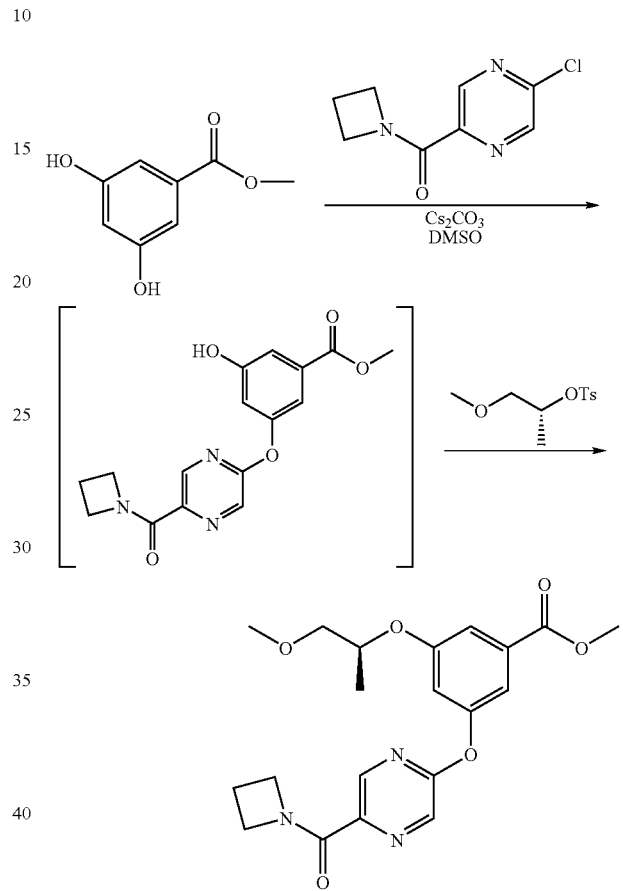

To a clean, dry, suitably serviced flask (flask A) fitted with overhead stirrer, thermometer, condenser, and nitrogen line was added methyl 3,5-dihydroxybenzoate (1.0 eq), 2-(azetidin-1-ylcarbonyl)-5-chloropyrazine (1.0 eq), cesium carbonate (3.5 eq), and dimethylsulfoxide (9.4 vols) under a nitrogen atmosphere. The reaction vessel was heated to 45° C. under a nitrogen atmosphere for at least 14 hours. (1R)-2-Methoxy-1-methylethyl 4-methylbenzenesulfonate (1.3 eq) was added over 45 minutes. The mixture was agitated at 45° C. for at least 14 hours then cooled to 22° C. and iso-propylacetate (10 vols) added. Water (12 vols) was added over 25 minutes at 25° C., and the mixture was agitated for 15 minutes at 22° C. The organic layer was separated off, after which the aqueous layer was re-extracted with (2×5 vols) iso-propylacetate. The iso-propyl acetate layers were combined and water (8 vols) was added. The mixture was agitated at 22° C. for 30 minutes. The aqueous layer was separated off and discarded. This process was repeated. The organic layer was distilled under vacuum to constant weight.

Meanwhile neutral alumina (18 weight eq) was mixed in a flask with iso-propyl acetate (4.5 vols) and heptane (11.2 vols). This mixture was added to a large chromatography column and the reaction mixture compressed on the column.

The mobile organic layer was diluted with iso-propyl acetate (0.2 vols) and heptane (0.4 vols). The mobile organic layer was then added to the column and eluted sequentially with 1:4 v/v iso-propyl acetate/heptane (50 vols), 1:3 v/v iso-propyl acetate/heptane (20 vols) and 6:4 v/v iso-propyl acetate/heptane (100 vols). Fractions were analysed by TLC, and fractions that contained clean product evaporated on the rotary evaporator to give the title compound as a thick oil in 59% corrected yield. $^1$H NMR (400 MHz, DMSO): δ 8.62 (s, 1H), 8.50 (s, 1H), 7.34 (s, 1H), 7.30 (s, 1H), 7.17 (s, 1H), 4.68-4.64 (m, 1H), 4.54-4.50 (t, 2H), 4.07-4.03 (t, 2H), 3.81 (s, 3H), 3.49-3.41 (m, 2H), 3.25 (s, 3H), 2.29-2.21 (m, 2H), 1.20-1.18 (d, 3H)

Preparation of (1R)-2-methoxy-1-methylethyl 4-methylbenzenesulfonate

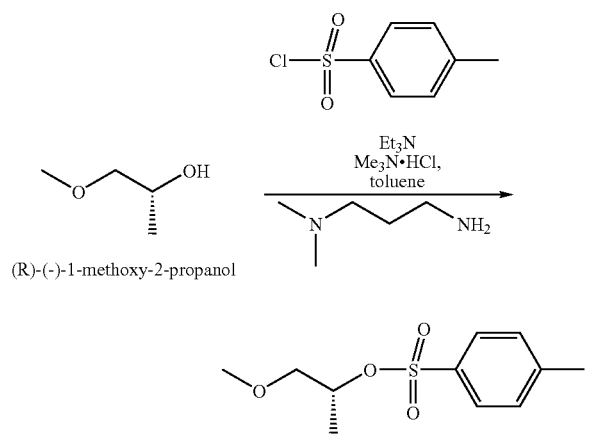

To a flask was added under a nitrogen atmosphere trimethylamine hydrochloride (0.1 eq), tosyl chloride (1.3 eq) and toluene (5 vols) and the reaction mixture agitated to form an oily slurry. The slurry was cooled to −5° C. (2R)-1-Methoxypropan-2-ol (1.0 eq) was added drop-wise over 30 minutes. Toluene (2.5 vols) was added as a wash followed by triethylamine (1.5 eq), which was added drop-wise via addition funnel over 30 minutes maintaining the reaction temperature<8° C. Further toluene (2.5 vols) was added as a wash and the reaction mixture held at −5° C. to 5° C. for 4.5 hours. N,N-Dimethyl-1,3-propane-diamine (0.3 eq) was added over 10 minutes at −5° C. The mixture was agitated at −5° C. to 5° C. for 30 minutes. Then 2N hydrochloric acid (0.55 eq) and 70 ml water were added. The mixture was agitated for 30 minutes at 22° C. and the aqueous layer was separated off and discarded. The mixture was washed twice more with water (10 vols each wash) and after separation of the aqueous wash, the toluene layer was distilled to an oil on the rotary evaporator. Toluene (20 vols) was added to the oil and the solution evaporated to give the title compound as a dry light brown oil. Yield (corrected for assay) 93-97%.

$^1$H NMR (400 MHz CDCl$_3$): δ 7.78-7.75 (d, 2H), 7.45-7.43 (d, 2H), 4.66-4.62 (m, 1H), 3.35-3.26 (m, 2H), 3.16 (s, 3H), 2.4 (s, 3H), 1.13-1.11 (d, 3H)

Preparation of methyl 3-hydroxy-5-[(phenylcarbonyl)oxy]benzoate

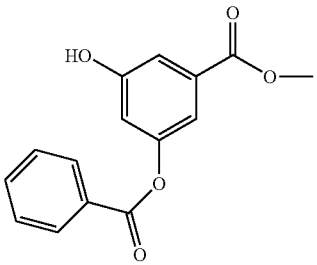

To a flask fitted with thermometer, condenser, overhead stirrer, pH probe and nitrogen line was added methyl-3,5-dihydroxybenzoate (1.0 eq), sodium phosphate mono-basic monohydrate (0.46 eq) and water (10.5 vols) under a nitrogen atmosphere. The temperature was adjusted to 20° C.±3° C. 10% w/w Sodium hydroxide was added to adjust the pH to pH 7.8±0.2. Benzoyl chloride (1.0 eq) was added drop-wise in small portions over 1-2 hours, and sodium hydroxide was added concurrently drop-wise in small portions over the same time period to maintain the reaction in a pH range of pH 7.8±0.2 and at a reaction temperature of 20° C.±3° C. The crude reaction mixture was agitated for a further 30 minutes, filtered, and then washed with 4 vols of a solution prepared from water (4 vols), sodium phosphate mono-basic monohydrate (0.05 eq), and adjusted to pH7.5 with 10% w/w sodium hydroxide. The crude solid was then washed with 4 vols of a solution prepared from water (4 vols), sodium phosphate mono-basic monohydrate (0.05 eq), and adjusted to pH6.5 with 10% w/w sodium hydroxide. The crude solid was then dissolved in iso-propyl acetate (8 vols) and water (2 vols) and the mixture agitated for at least 30 minutes to ensure the solid had dissolved. The mixture was filtered through a CUNO™ filter to remove a small amount of brown solid. The aqueous layer was separated off. Water (2 vols) was added to the organic layer and the batch agitated for at least 30 minutes. The aqueous layer was separated off and the organic layer was vacuum distilled, keeping the batch temperature below 40° C. to reduce the volume to 5-6 vols. Toluene was added then added (5 vols) and the mixture was vacuum distilled keeping the batch temperature below 40° C., reducing the volume to approximately 3.5 vols. The mixture was cooled to 15° C.±3° C. and agitated at this temperature for at least 30 minutes, then filtered, and the solid washed with toluene (1 vol). The product was dried at 20° C.-40° C. to give the desired product as a solid (corrected yield 40%-70%).

$^1$H NMR δ (400 MHz; CDCl$_3$): 8.21-8.18 (d, 2H), 7.67-7.63 (t, 1H), 7.54-7.49 (t, 2H), 7.44 (d, 2H), 6.98-6.96 (t, 1H), 6.7 (bs, 1H), 3.90 (s, 3H).

Alternatively methyl 3-hydroxy-5-[(phenylcarbonyl)oxy]benzoate may be made by the following process To a flask fitted with thermometer, condenser, overhead stirrer, pH probe and nitrogen line was added methyl-3,5-dihydroxybenzoate (1.0 eq), 325 mesh potassium carbonate (3.0 eq) and dimethylformamide (DMF) (4 vols) under a nitrogen atmosphere. The mixture was heated to 47° C. for 1 hour, then benzoyl chloride (1.0 eq) was added slowly drop-wise via syringe pump over approximately 2 hours. Further benzoyl chloride was added (0.1 eq) over 20 minutes via syringe pump. The reaction mixture was held for 1.5 hours, then water (10 vols) and iso-propyl acetate (6 vols) were added. The reaction mixture was agitated for 30 minutes and then the layers were separated. The aqueous layer was re-extracted with a further charge of iso-propyl acetate (6 vols). The batch was separated, and the combined organic layers were washed with saturated brine (6 vols), then with a solution of 0.1N hydrochloric acid/brine. The iso-propyl acetate was distilled to dryness on the rotary evaporator. Iso-propyl acetate (6 vols) was added, and distilled to dryness on the rotary evaporator. Toluene (6 vols) was added and distilled to dryness on the rotary evaporator. Toluene (3.5 vols) was added and the reaction slurried for 30 minutes. The solid was filtered off and dried at 20° C.-40° C. to give the desired product as a solid (corrected yield 72%).

Alternative Preparation of methyl 3-hydroxy-5-[(phenylcarbonyl)oxy]benzoate

To an inerted flask fitted with thermometer, condenser, overhead stirrer, pH probe and nitrogen line was charged methyl 3,5-dihydroxy benzoate and suspended in 10 vol water. The pH of the suspension was adjusted to 8.0 using an aqueous solution of 2.5% lithium hydroxide and 2.5% potassium carbonate. A solution of benzoyl chloride (1.0 eq.) in 2 vol toluene was added at such a rate that the internal temperature could be maintained between 20 and 22° C. The pH of the solution was maintained between 7.9 and 8.1 by simultaneous addition of an aqueous solution of 2.5% lithium hydroxide and 2.5% potassium carbonate (approximately 5 vol). The resulting suspension was agitated for further 60 minutes at 20-22° C. and then filtered. The filter cake was washed twice with water (2 vol each) and pulled dry. The crude product obtained was then dissolved in isopropyl acetate (8 vol) before Diatomaceous earth was added and the slurry was stirred for 1 h. Following filtration of the to suspension the product is then solvent-swapped from isopropyl acetate into toluene (5 vol) by vacuum distillation maintaining the internal temperature at or below 45° C. The resulting suspension was cooled to 15° C., agitated for 1 h and then filtered. After washing the filter cake with 1 vol toluene the product was dried to constant weight yielding typically 75-80% of the title product at >98% purity.

Preparation of (1R)-2-methoxy-1-methylethyl 4-methylbenzenesulfonate

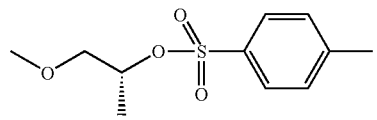

To a flask fitted with overhead stirrer, condenser, thermometer and nitrogen line was added trimethylamine hydrochloride (0.1 eq), tosyl chloride (1.3 eq) and toluene (5 vols) under a nitrogen atmosphere and the reaction mixture agitated to form an oily slurry. The slurry was cooled to −5° C., then (2R)-1-methoxypropan-2-ol (1.0 eq) was added drop-wise over 30 minutes. Toluene (2.5 vols) was added as a line wash followed by triethylamine (1.5 eq), which was added dropwise via addition funnel over 30 minutes maintaining the reaction temperature<8° C. Further toluene (2.5 vols) was added as a line wash and the reaction mixture held at −5° C. to 5° C. for 4.5 hours. N,N-dimethyl-1,3-propane-diamine, (0.3 eq) was added over 10 minutes at −5° C. The reaction mixture was agitated at −5° C. to 5° C. for 30 minutes, then 2N hydrochloric acid (0.55 eq) and 70 ml water were added. The reaction mixture was agitated for 30 minutes at 22° C. and the aqueous layer was separated off and discarded. The mixture was washed twice more with water (10 vols each wash) then the toluene layer was distilled to an oil on the rotary evaporator. Toluene (20 vols) was added to the oil and the solution evaporated to an oil to give the title compound as a dry light brown oil. Yield corrected for assay 93-97%. $^1$H NMR δ (400 MHz CDCl$_3$): 7.78-7.75 (d, 2H), 7.45-7.43 (d, 2H), 4.66-4.62 (m, 1H), 3.35-3.26 (m, 2H), 3.16 (s, 3H), 2.4 (s, 3H), 1.13-1.11 (d, 3H).

Preparation of (1R)-2-methoxy-1-methylethyl 4-(trifluoromethyl)benzenesulfonate)

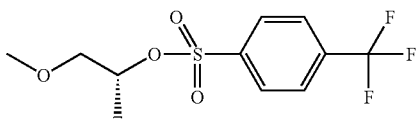

To a flask was added 4-trifluoromethylsulfonylchloride (1.3 eq) and toluene (10 vols), the reaction mixture was cooled to 5° C., then (2R)-1-methoxypropan-2-ol (1.0 eq) was added at 5° C. Trimethylamine hydrochloride (0.1 eq) was added at 5° C., then triethylamine (1.5 eq) added slowly drop-wise over 50 minutes maintaining the reaction temperature between 5-12° C. After holding for approximately 18 hours at 5° C., the reaction was quenched by the dropwise addition of 3-dimethylaminopropane (0.3 eq) over minutes at 5° C. The reaction mixture was stirred for 2 hours at 5° C., then water (5 vols) added at 5° C., then 5N hydrochloric acid (2 vols) was added slowly at 5° C. The reaction mixture was warmed to 20° C., water (1 vol) was added followed by toluene (10 vols). The reaction mixture was warmed to 30° C., then the aqueous layer separated off and discarded. Water (5 vols) was added and the reaction mixture agitated for 30 minutes, then the water layer separated off and discarded. 8% w/w Sodium carbonate (4 vols) was added, the reaction mixture agitated for 30 minutes, then the water layer separated off and discarded. Water (5 vols) was added, the batch agitated for 30 minutes, then the water layer separated off and discarded. This water wash was repeated twice. The organic layer was evaporated to an oil on the rotary evaporator. Toluene was added and the organic layer was evaporated to an oil on the rotary evaporator. This process was repeated to give the desired product as a yellow oil (corrected yield 97%). $^1$H NMR δ (400 MHz CDCl$_3$) 8.07-8.05 (d, 2H), 7.82-7.80 (d, 2H), 4.84-4.80 (m, 1H), 3.44-3.35 (m, 1H), 3.19 (s, 3H), 1.35-1.33 (d, 3H).

Preparation of 3-hydroxy-5-[(1S)-2-methoxy-1-methylethoxy]benzoic acid

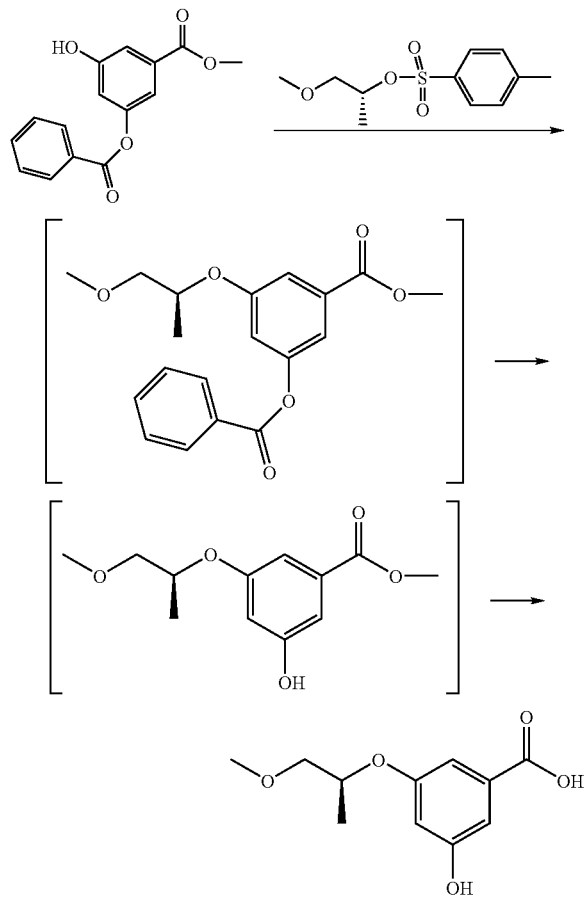

To a flask fitted with overhead stirrer, condenser, thermometer and nitrogen line was added methyl 3-hydroxy-5-[(phenylcarbonyl)oxy]benzoate (1.0 eq), cesium carbonate (1.5 eq) and dimethylsulfoxide (7.0 vols) under a nitrogen atmosphere. The batch was heated to 40-45° C. (1R)-2-methoxy-1-methylethyl 4-methylbenzenesulfonate (1.3 eq) was added slowly dropwise over at least 90 minutes maintaining reaction temperature at 40-45° C. The reaction mixture was held for at least 8 hours and then was cooled to 15±4° C. Iso-propyl acetate (4.0 vols) was added followed by water (5.0 vols), keeping the reaction temperature below 25° C. The reaction mixture was agitated for approximately 15 minutes and then the layers were separated. The organic phase was retained. The aqueous phase was re-extracted with further iso-propyl acetate (3 vols). The reaction mixture was agitated for approximately 15 minutes and then the layers separated. This process was repeated with further isopropyl acetate and the organic phases were combined and then washed with water (3 vols). After approximately 15 minutes agitation the layers were separated, and water (3 vols) was added to the organic layer. After approximately 15 minutes agitation the layers were separated and the organic layer was vacuum distilled at 40° C. until no more solvent could be distilled. Methanol (7 vols) was added, then sulphuric acid (0.8 eq) was added and the mixture was heated to reflux for at least 16±4 hours. The reaction mixture was vacuum distilled at 40° C. until a pot volume of 2.5-3 vols was achieved. Toluene (4 vols) was added to the flask, and vacuum distillation continued at 35° C. until a pot volume of 4.0 vols was achieved. The mixture was cooled to 20±5° C. Water (15 vols) was added to the reaction mixture and the mixture agitated at 20±5° C. for at least 15 minutes. The batch was separated and the organic layer was cooled to 0-5° C., before 0.5M sodium hydroxide (1.0 eq) was added slowly keeping the batch temperature below 5° C. The vessel was agitated for 15 minutes and then separated. The aqueous layer was retained and the organic layer was treated with 0.5M sodium hydroxide (1.0 eq; added slowly keeping the batch temperature below 5° C.). The vessel was agitated for 15 minutes and then the layers were separated. The aqueous layers were combined and toluene (3 vols) added slowly keeping the batch temperature below 5° C. The vessel was agitated for 15 minutes and then separated. The aqueous layer was warmed to 25±5° C., and 33% w/w sodium hydroxide added (0.5 eq). After 2 hours stirring, 37% w/w hydrochloric acid (2.1 eq) was added to adjust the pH to pH 2. Methyl tert-butyl ether (3 vols) was added, the mixture was agitated for 15 minutes, then the layers separated. The organic layer was retained. The aqueous layer was re-extracted with MTBE (3 vols) and the combined organic layers were distilled under vacuum at 35° C. to a pot volume of approximately 3 vols, collecting 3 vols distillates. Toluene (5 vols) was added, and the batch temperature adjusted to 50° C. Water (1 vol) was added and the batch agitated for at least 15 minutes at this temperature then the layers were separated. The organic layer filtered through a filter then distilled at 35° C. until the mixture became turbid. The material was cooled to 20° C., seeded with 3-hydroxy-5-[(1S)-2-methoxy-1-methylethoxy]benzoic acid and agitated at this temperature for 3 hours. The mixture was then distilled under vacuum at 25° C. is removing further MTBE, and then cooled to 5° C. for at least 2 hours. The mixture was filtered, and the solid was washed with toluene (1 vol) at 20° C. The batch was dried with vacuum or under a stream of nitrogen until constant weight was attained at 20° C. After drying, the title compound was obtained as a solid (corrected yield typically 40-50%). $^1$H NMR δ (400 MHz DMSO): 12.82 (bs, 1H), 9.74 (bs, 1H), 6.95 (bs, 1H), 6.91 (bs, 1H), 6.56-6.55 (t, 1H), 4.59-4.52 (m, 1H), 3.5-3.41 (m, 2H), 3.28 (s, 3H), 1.21-1.19 (d, 3H).

Alternative Preparation of 3-hydroxy-5-[(1S)-2-methoxy-1-methylethoxy]benzoic acid Methyl 3-hydroxy-5-[(phenylcarbonyl)oxy]benzoate (1.0 eq.), (R)-1-methoxy-2-propanol (1.25 eq.) and triphenylphosphine (1.25 eq.) were suspended in toluene (10 vol). Diisopropyl azodicarboxylate (1.25 eq.) was added at a batch temperature of between 0 and 5° C. over ~2 h. The mixture was allowed to warm to room temperature and was stirred for further 30 min. at this temperature. The resulting suspension was filtered to remove the bulk of the triphenylphosphine oxide formed and the filter cake was washed with toluene (1.5 vol). To the combined toluene fractions containing the resulting methyl 3-[(1S)-2-methoxy-1-methylethoxy]-5-[(phenylcarbonyl)oxy]benzoate was added sodium methylate (0.8 eq.) at a batch temperature of between 20 and 30° C. and the mixture was stirred to 1 h. The solution of the resulting methyl 3-hydroxy-5-[(1S)-2-methoxy-1-methylethoxy]-benzoate was then extracted twice with KOH 0.25 M (3.5 vol each) at a batch temperature of between 0 and 5° C. KOH was then added (1 eq.) to hydrolyse the ester moiety and the batch was stirred for 1 h at a temperature of between 20 and 30° C. The pH of the aqueous phase is then adjusted to 1.5 using conc. hydrochloric at a batch temperature of <30° C. Crude 3-hydroxy-5-[(1S)-2-methoxy-1-methylethoxy]benzoic acid was subsequently extracted into MTBE (2×3 vol) before activated charcoal was added. The batch was stirred for 10 minutes and then filtered. The batch was reduced to 3 pot volumes by distillation at a batch temperature of <45° C. Toluene (4 vol) and heptane (1 vol) were added and vacuum distillation was continued at a batch temperature of <50° C. until no further MTBE was collected. The batch was cooled to a temperature of <40° C., seeded and further cooled to a batch temperature of between 28 and 32° C. The resulting suspension was stirred for 1 h at this temperature before being further cooled to 5 to 10° C. After 2 h stirring at 5 to 10° C. the batch was filtered and washed with cold toluene (1 vol.). Drying at <60° C. furnished 3-hydroxy-5-[(1S)-2-methoxy-1-methylethoxy]benzoic acid in >99% purity as colourless solid with a melting point of 95° C. in a typical yield between 65 and 70% from methyl 3-hydroxy-5-[(phenylcarbonyl)oxy]benzoate.

Methyl 3-[(1S)-2-methoxy-1-methylethoxy]-5-[(phenylcarbonyl)oxy]benzoate $^1$H NMR (400 MHz, CDCl$_3$) δ 8.21-8.17 (d, 2H), 7.66-7.62 (t, 1H), 7.54-7.49 (m, 4H), 7.03-7.02 (t, 1H), 4.64-4.60 (m, 1H), 3.9 (s, 3H), 3.61-3.49 (m, 2H), 3.45 (s, 3H), 1.35-1.33 (d, 3H)
$^{13}$C NMR data (100.55 MHz, CDCl$_3$) δ 166.2, 164.91, 158.88, 151.79, 133.87, 132.25, 130.28, 129.28, 128.71, 115.6, 114.95, 114.27, 75.7, 73.83, 59.45, 52.44, 16.72.

Methyl 3-hydroxy-5-[(1S)-2-methoxy-1-methylethoxy]benzoate $^1$H NMR (400 MHz, DMSO) δ 6.93 (s, 1H), 6.90 (s, 1H), 6.57 (bs, 1H), 4.55-4.51 (m, 1H), 3.79 (s, 3H), 3.47-3.41 (m, 2H), 3.26 (s, 3H), 1.18-1.17 (d, 3H)

Preparation of 3-hydroxy-5-[(1S)-2-methoxy-1-methylethoxy]benzoic acid (t-butylamine salt)

To a flask fitted with overhead stirrer was added 3-hydroxy-5-[(1S)-2-methoxy-1-methylethoxy]benzoic acid (1.0 eq) and acetonitrile (6 vols). Tert-butylamine (1.0 eq) was added at 22° C., followed by acetonitrile (3 vols). After stirring for at least 5 hours, the reaction mixture was filtered and dried in a vacuum oven to give the title compound as a crystalline white solid (73.6%). $^1$H NMR (400 MHz DMSO) δ: 6.90 (bs, 1H), 6.85 (s, 1H), 6.30-6.29 (t, 1H), 4.47-4.43 (m, 1H), 3.47-3.35 (m, 2H), 3.09 (s, 3H), 1.22 (s, 9H), 1.17-1.16 (d, 3H). Melting point by Differential Scanning Calorimetry (DSC) 154.7° C.

Preparation of 3-hydroxy-5-[(1S)-2-methoxy-1-methylethoxy]benzoic acid (potassium salt)

KOH liquor (1.04 eq. of 50.4 wt %) was added to a stirred, nitrogen sparged solution of 3-hydroxy-5-[(1S)-2-methoxy-1-methylethoxy]benzoic acid (1 eq.) in undried 1-propanol (4.87 vol.). At the end of the addition, water (0.33 vol.) and toluene (3.43 vol.) were separately added to the resulting slurry. The jacket temperature was raised to 67° C. before being subjected to the following cooling profile: 67° C. to 64° C. over 3 h, 64 to 57° C. over 3 h, 57 to 45° C. over 3 h, and 45 to 20° C. over 3 h. 6 h after the end of this ramp, the jacket temperature was lowered to 0° C. over 3 h, the jacket was foil wrapped and desupersaturation was allowed to complete overnight (>6 h). The slurry was isolated by filtration through an 11 micron filter paper. The cake was sequentially washed twice with an equal weight of an ice-cold solution of toluene (41.79 wt %) in 1-propanol. The cake was dried in a 40° C. house vacuum oven to give 3-hydroxy-5-[(1S)-2-methoxy-1-methylethoxy]benzoic acid potassium salt as tri-hydrate in a typical yield of 93% of theoretical yield.
$^1$H NMR (400 MHz, d$_6$-DMSO) 9.05 (1H, br s), 6.86-6.83 (2H, m), 6.18 (1H, dd, J=2.3, 2.3), 4.44 (1H, qdd, 6.2, 5.1, 5.1), 3.48-3.33 (8H, m), 3.28 (3H, s), 1.18 (3H, d, J=2.3)

Other salts of 3-hydroxy-5-[(1S)-2-methoxy-1-methylethoxy]benzoic acid, e.g. sodium, calcium or magnesium salts, were formed in a similar way using appropriate bases, e.g. sodium hydroxide, magnesium hydroxide or calcium hydroxide or by salt exchange for example by using potassium acetate or potassium 2-ethyl hexanoate (in propan-2-ol) for the potassium salt or using calcium bis-(2-ethylhexanoate) for the calcium salt.

Process for enzymatic conversion of (methyl 3-[(1S)-2-methoxy-1-methylethoxy]-5-[(phenylcarbonyl)oxy]benzoate to methyl 3-hydroxy-5-[(1S)-2-methoxy-1-methylethoxy]benzoate To a flask fitted with thermometer and magnetic stirrer was added (methyl 3-[(1S)-2-methoxy-1-methylethoxy]-5-[(phenylcarbonyl)oxy]benzoate) (1.0 eq), and tert-butanol (90 vols) followed by addition of either water (10 vols) or pH7 buffer (10 vols). Enzyme 1 wt eq (either AE 01 Lipase Cl or Alphamerix AE-02) was added and the reaction agitated at 36° C. for several days (such as 7 days) until the reaction was complete.

Preparation of 3-{[5-(azetidin-1-ylcarbonyl)pyrazin-2-yl]oxy}-5-[(1S)-2-methoxy-1-methylethoxy]benzoic acid

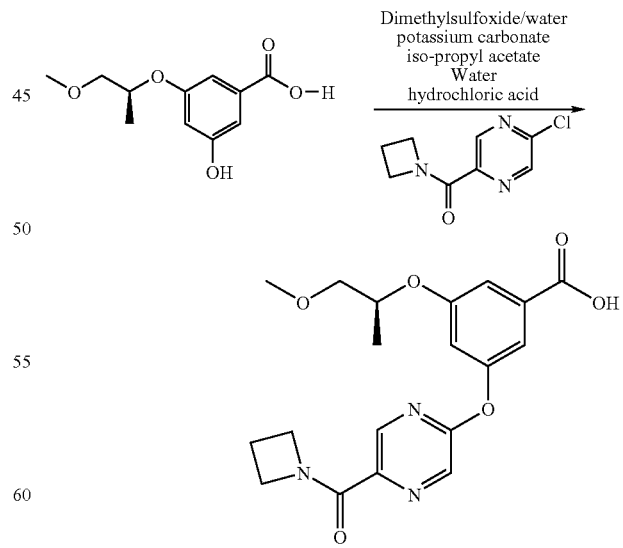

To a clean dry flask fitted with thermometer, condenser, overhead stirrer and nitrogen line was added 3-hydroxy-5-[(1S)-2-methoxy-1-methylethoxy]benzoic acid* (1.0 eq), potassium carbonate (2.5 eq), dimethylsulfoxide (3 vols) and water (1.0 vols) under a nitrogen atmosphere. The resulting mixture was heated to 45° C.-55° C. for at least one hour. 2-(Azetidin-1-ylcarbonyl)-5-chloropyrazine (1.05 eq) was dissolved in dimethylsulfoxide (5.0 vols) at about 40° C.-50° C. The solution of 2-(azetidin-1-ylcarbonyl)-5-chloropyrazine in DMSO was added drop-wise via syringe pump to the above reaction mixture over 1-4 hours maintaining the reaction temperature at 45° C.-55° C. The reaction was stirred for 16 hours at 45° C.-55° C. The bath was cooled to 22±3° C. Water (8 vols) was added, followed by iso-propyl acetate (10 vols). The contents were agitated at 22° C. for 15 minutes then the layers were separated The aqueous layers was treated with iso-propylacetate (10 vols) and the mixture agitated at 22±3° C. for at least 15 minutes. The layers were separated and the aqueous layer was treated again with iso-propylacetate in the same manner. The layers were separated, the organic layer was discarded and 5N hydrochloric acid (~4.4 eq) was added drop-wise over at least 30 minutes to the aqueous layer to a pH end-point of pH 3-0-pH4.0 whilst maintaining the reaction temperature at 22±3° C. Iso-propylacetate (10 vols) was then added and the mixture heated to 75° C. The mixture was agitated at this temperature for at least 30 minutes, then the temperature was adjusted to 70° C. and the layers were separated. The organic layer was retained, and the aqueous layer treated with iso-propylacetate (10 vols) and the mixture heated to 75° C. The mixture was agitated at this temperature for at least 30 minutes, then the temperature was adjusted to 70° C. and the layers separated. The organic layer was retained, and the aqueous layer discarded. The combined organic layers from the previous 2 separations were reheated to reflux for dissolution. Water (5 vols) was added and the mixture stirred at 70-75° C. for at least 15 minutes. The batch temperature was adjusted to 70° C. and the aqueous layer separated off and discarded. This process was repeated twice with a further 5 vols of water at each time. The organic layer was set to distil at atmospheric pressure to a pot volume of 4 vols. Iso-propyl acetate (8 vols) was added and the batch set to distil to a pot volume of approximately 4 vols. The batch was cooled to 22° C. over 2 hours, the batch was agitated at 22° C. for 3 hours, then cooled to 0° C., the mixture was held at 0° C. for 5 hours, then filtered, and the solid washed with iso-propylacetate (20 ml, 4 vols). After drying in the vacuum oven at 50° C. overnight, the desired product was obtained as a solid (corrected yield 85-90%). $^1$H NMR δ (400 MHz DMSO): 8.66 (s, 1H), 8.55 (s, 1H), 7.36 (s, 1H), 7.31 (s, 1H), 7.16 (s, 1H), 4.71-4.65 (m, 1H), 4.58-4.54 (t, 2H), 4.11-4.07 (t, 2H), 3.52-3.41 (m, 2H), 3.29 (s, 3H), 2.33-2.26 (m, 2H), 1.24-1.19 (d, 3H)

*Alternatively, salts of this acid may be used in this procedure, either directly or after transformation into the free acid by cracking the salt by appropriate method, eg: acidification and extraction, adding NaOH then distilling, or any other process known in the art.

Preparation of 3-{[5-(azetidin-1-ylcarbonyl)pyrazin-2-yl]oxy}-5-[(1S)-2-methoxy-1-methylethoxy]benzoic acid Alternative Method 3-Hydroxy-5-[(1S)-2-methoxy-1-methylethoxy]benzoic acid (5.00 g, 22.10 mmol) and tetra n-butyl phosphonium chloride (6.53 g, 22.1 mmol) were suspended in 2-methyltetrahydrofuran (25 ml, 5 vol rel. to the benzoic acid) and 22 mL water at ambient temperature under nitrogen. Solid potassium carbonate (27.98 g, 202.4 mmol) was charged portion-wise with vigorous mechanical stirring. At the end of addition KOH liquor (2.46 g 50% wt/wt in water, 22.1 mmol) was added before the biphasic slurry was heated to 50° C. Once the temperature had stabilised, 2-(azetidin-1-ylcarbonyl)-5-chloropyrazine (4.586 g, 23.21 mmol) was charged portion-wise over 40 minutes and the mixtures was stirred over night under nitrogen at 50° C. The phases were split and the lower aqueous phase was run off 25 ml of toluene and 50 mL water were added to the remaining dark red organic phase. The pH of the aqueous phase was then adjusted to 7.0 using conc. hydrochloric acid. The jacket temperature was adjusted to 20° C. and the phases were separated again (the lower aqueous phase was run off and retained; the upper organic phase was discarded). The aqueous phase was washed with more toluene (25 mL). After phase separation the toluene phase was removed again. The pH of the retained aqueous phase was adjusted to 2.1 using 5M hydrochloric acid solution (7.1 mL). Isopropyl acetate (34.9 g) was charged and the jacket temperature was raised to 80° C. Equilibration was performed with the jacket temperature set to 80° C. After phase split the lower aqueous phase was run off again and back-extracted with more isopropyl acetate (17.4 g). The organic phases were combined and homogenised at 80° C. before being washed with water (10 mL). The organic phase was dried by azeotropic distillation under slight vacuum at constant batch volume (batch partially crystallised). The suspension was cooled to 0° C. over 13.5 h and the batch was isolated by filtration followed by a cake-wash with isopropyl acetate (17.4 g). After drying at 40° C. in a vacuum oven overnight 5.25 g at 96% strength (59% corrected yield) of the desired product was obtained as white solid.

3-{[5-(Azetidin-1-ylcarbonyl)pyrazin-2-yl]oxy}-5-[(1S)-2-methoxy-1-methylethoxy]-N-(5-methylpyrazin-2-yl)benzamide

A

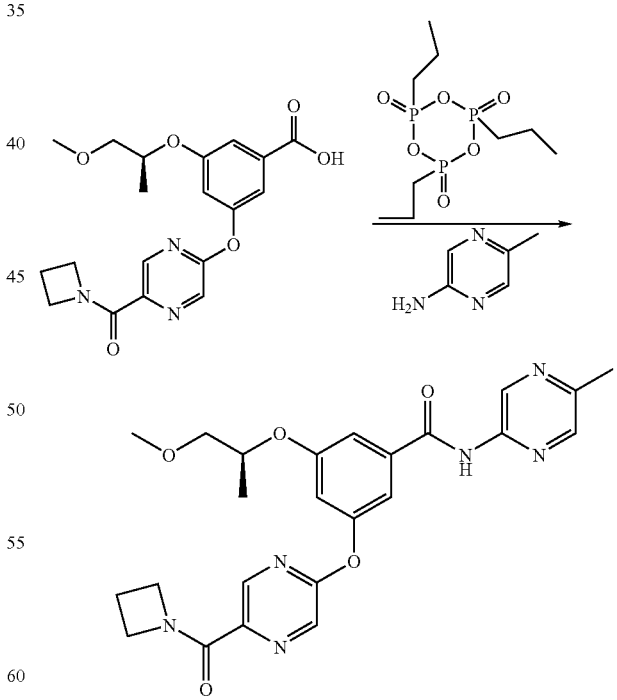

To a flask fitted with overhead stirrer, thermometer, condenser, and nitrogen line was added 3-{[5-(azetidin-1-ylcarbonyl)pyrazin-2-yl]oxy}-5-[(1S)-2-methoxy-1-methylethoxy]benzoic acid (1.0 eq), 5-methylpyrazin-2-amine (1.12 eq) and 2-methyltetrahydrofuran (4.4 vols) under a nitrogen atmosphere. The mixture was cooled to 5° C., and then N-methylmorpholine (5.0 eq) added drop-wise over at least 15 minutes maintaining the temperature at 5±5° C. 1-Propanephosphonic acid cyclic anhydride (T3P) (as 50% w/w solution in ethyl acetate) (2.5 eq) was added drop-wise over at least 15 minutes maintaining the temperature at 5±5° C. The mixture was heated to reflux for at least 16 hours then cooled to 22±5° C. Water (4.0 vols) was added to the reaction mixture, followed by 2-methyltetrahydrofuran (4.0 vols). After agitating for 30 minutes, the mixture was separated. The upper organic layer was retained and the aqueous layer treated with 2-methyltetrahydrofuran (4.0 vols). After agitating for 30 minutes, this mixture was separated. The organic layers were combined and further 2-methyltetrahydrofuran (6.0 vols) was then added. The mixture was agitated, and 1.0N hydrochloric acid (4.0 vols) was added. The mixture was agitated for at least 30 minutes at 22±5° C., and the layers were then separated. The organic layer was treated with 1.0N hydrochloric acid (4.0 vols) then the mixture was agitated for at least 30 minutes at 22±5° C., then the layers were separated. The organic layer was treated with 5% w/w sodium hydrogen carbonate (4.0 vols). The mixture was agitated for at least 30 minutes at 22±5° C., the layers were separated. The organic layer was treated again with 5% w/w sodium hydrogen carbonate (4.0 vols) following the same procedure, and then with water (4.0 vols) following the same procedure. The organic layer was then distilled at atmospheric pressure to a pot volume of 4.7 vols. Methyl iso-butylketone (10 vols) was added, and the batch distilled at atmospheric pressure to a pot volume of 4.68 vols. Methyl iso-butylketone (10 vols) was added, and the batch distilled at atmospheric pressure to a pot volume of 4.68 vols. The batch was cooled to 70° C., heptane (2.02 vols) was added slowly drop-wise over at least 30 minutes maintaining the reaction temperature at 70±5° C. The mixture was cooled to 60° C., and seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide Form 1, agitated at 60° C. for 1 hour, cooled to 50° C. at 0.1° C., agitated at 50° C. for 140 minutes, then cooled to 22° C. at 0.1° C./minute. The mixture was held at 22° C. for at least 12 hours. Heptane (5.06 vols) was then added—drop-wise over at least 120 minutes maintaining the batch temperature at a temperature at 22±5° C. The mixture was cooled to 0° C. at 0.1° C./minute then held at 0° C. for at least 12 hours and then filtered. The isolated solid was washed with a mixture of methyl iso-butylketone (1.0 vols) and heptane (3.0 vols) pre-chilled to 0° C. The solid was dried at 40° C. After drying in the vacuum oven at 40° C. overnight, the desired product was obtained as a solid (corrected yield 85%. $^1$H NMR δ (400 MHz DMSO) 11.04 (s, 1H), 9.26 (s, 1H), 8.68 (s, 1H), 8.57 (s, 1H), 8.36 (s, 1H), 7.56 (s, 1H), 7.46 (s, 1H), 7.12 (s, 1H), 4.81-4.77 (m, 1H), 4.58-4.54 (t, 2H), 4.11-4.07 (t, 2H), 3.55-3.47 (m, 2H), 3.3 (s, 3H), 2.48 (s. 3H), 2.34-2.26 (m, 2H), 1.26-1.25 (d, 3H).

3-{[5-(Azetidin-1-ylcarbonyl)pyrazin-2-yl]oxy}-5-[(1S)-2-methoxy-1-methylethoxy]-N-(5-methylpyrazin-2-yl)benzamide

B

3-{[5-(Azetidin-1-ylcarbonyl)pyrazin-2-yl]oxy}-5-[(1S)-2-methoxy-1-methylethoxy]-benzoic acid (1.0 eq), (1.00 mol eq), 5-methylpyrazin-2-amine (1.12 mol eq) and 2-methyltetrahydrofuran (2.00 rel vols) were charged to a vessel and stirred at 20° C. N-methylmorpholine (5.00 mol eq) was added followed by a line-wash with 2-methyl-tetrahydrofuran (0.50 rel vols). A 50 wt % solution of 1-propanephosphonic acid cyclic anhydride (T3P) in 2-methyltetrahydrofuran (1.70 mol eq) was charged followed by a line wash with 2-methyltetrahydrofuran (0.50 rel vols). The resulting mixture was heated to 78° C. over 30 minutes and the clear yellow solution was held at 78° C. for roughly 22 hours, then checked for acceptable conversion. At the end of reaction the solution was further diluted with 2-methyltetrahydrofuran (7.00 rel vols) and the temperature was adjusted to 45° C. 5 wt % aq. sodium bicarbonate solution (6.00 rel vols) was slowly added over 30 mins to the stirring solution causing gas evolution. After 15 minutes stirring was turned off and the phases were allowed to separate over 30 minutes. The lower aqueous phase was drained off 20 wt % aq. phosphoric acid (3.30 rel vols) was charged to the stirring organic phase. After 15 minutes stirring the phases were allowed to separate and the lower aqueous phase was drained off again. A mixture of 20 wt % aq. phosphoric acid (1.50 rel vols) and water (1.50 rel vols) was charged to the stirring organic phase. After 15 minutes, stirring was turned off and the mixture held overnight for phase separation. The lower (aqueous) phase was drained off again. 5 Wt % aq. sodium bicarbonate (4.50 rel vols) was added over at least 10 mins to the stirring solution. After phase separation the lower (aqueous) phase was run off again. The resulting solution was dried by azeotropic distillation to a concentration of approximately 241 mg/g, collecting around 0.48 rel vols of the lower distillate phase. Heptane (1.60 rel vols) was added over 10 mins to the dry solution at above 50° C. before the batch was cooled to 40° C. The solution was seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide (Form 1 Seed, 0.0010 rel wt) before an overnight temperature program was applied: held at 40° C. for 2 hrs; cooled to 35° C. at 0.1° C./min (50 minutes); held for 2 hours; cooled to 30° C. at 0.1° C./min (50 minutes); held for 2 hours; cooled to 0° C. at 0.1° C./min (300 minutes); and held for at least 2 hours. After crystallisation overnight, further heptane (4.1 rel vols) was added over 2.0 hours to reduce losses to liquors to <4.0 mg/mL. The suspension was then filtered followed by a line rinse with a pre-mixed solution of heptane (2.10 rel vols) and 2-methyltetrahydrofuran (0.90 rel vols) and transferred to a filtration apparatus?. The filter cake was dried to constant weight at 40° C. to furnish crude 3-{[5-(azetidin-1-ylcarbonyl)pyrazin-2-yl]oxy}-5-[(1S)-2-methoxy-1-methylethoxy]-N-(5-methylpyrazin-2-yl)benzamide in 86-89% of theory as Form I.

Process for crystallisation of 3-{[5-(azetidin-1-ylcarbonyl)pyrazin-2-yl]oxy}-5-[(1S)-2-methoxy-1-methylethoxy]-(5-methylpyrazin-2-yl)benzamide (as form 4) from 2-methyltetrahydrofuran/isohexane To a flask fitted with overhead stirrer, condenser, thermometer and nitrogen line was added a solution of 3-{[5-(azetidin-1-ylcarbonyl)pyrazin-2-yl]oxy}-5-[(1S)-2-methoxy-1-methylethoxy]-N-(5-methylpyrazin-2-yl)benzamide in 2-methyltetrahydrofuran under a nitrogen atmosphere. The solution was distilled at atmospheric pressure until a pot volume of 7 vols was obtained. Iso-hexane (3 vols) was added at 70° C., then cooled to 50° C. for 1 hour. The mixture was seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide (form 1) (5% wt/wt). The mixture was cooled to 0° C. at 0.1° C./minutes and left to agitate at 0° C. for at least 48 hours. The mixture was filtered and dried and left to dry on standing at 22° C. to give the title compound as an off white solid. Yield of isolated solid was 68% as form 4.

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide) (as form 6)

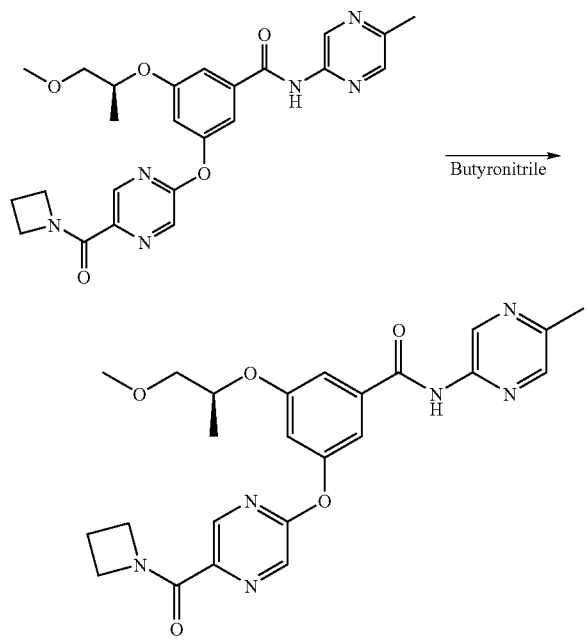

To a flask fitted with thermometer, condenser, overhead stirrer and nitrogen line was added 3-{[5-(azetidin-1-ylcarbonyl)pyrazin-2-yl]oxy}-5-[(1S)-2-methoxy-1-methylethoxy]-N-(5-methylpyrazin-2-yl)benzamide (1.0 eq) and butyronitrile (5.4 vols) under a nitrogen atmosphere. The batch was heated to 50° C. and filtered into another flask. The mixture was cooled to 45° C., and then seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide) (form 6) (0.075% w/w). The mixture was held at 45° C. for 3 hours, then cooled to 15° C. at 0.1° C./minute and held at 15° C. for at least 24 hours then filtered. The solid was washed with butyronitrile (2 vols) pre-chilled to 15° C. The solid was dried at 40° C. until the solvent level was <0.5% w/w. After drying in the vacuum oven at 40° C. overnight, the title compound was obtained as a solid (corrected yield 85%).

Preparation of 5-Chloropyrazine-2-carboxylic acid

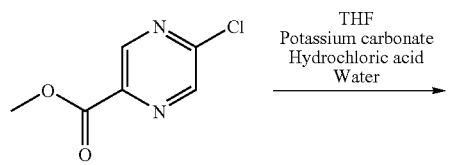

To a flask fitted with overhead stirrer, condenser, thermometer and nitrogen line was added methyl 5-chloropyrazine-2-carboxylate (1.0 eq) and tetrahydrofuran (4.92 vols) under a nitrogen atmosphere. The reaction mixture was agitated until all the solid had dissolved, then filtered into a second flask. Water (8.65 vols) was added to the reaction mixture and the mixture agitated for approximately 15 minutes. Potassium carbonate (2.1 eq) was added to the reaction mixture and the mixture agitated for 16 hours at 20-25° C. Then 32% w/w hydrochloric acid (3.76 eq) was added over 3 hours in small portions, keeping the reaction temperature 20-25° C., to a pH end point of pH2.2. The resultant slurry was heated to approximately 35-40° C. and then distilled under vacuum at this temperature distilling approximately 5.3 vols, to a final volume of approximately 9.3 vols. The mixture was then cooled to 20-25° C. over at least 2 hours, agitated for 10 hours at this temperature and then filtered. The solid was washed with water (2.8 vols), and the wet product produced dried at 35° C. in a vacuum oven. The desired product was obtained as a solid (corrected yield 91%) $^1$H NMR δ (400 MHz CDCl$_3$): 7.20 (1H, bs), 8.72 (1H, s), 9.21-9.21 (1H, m); m/z 157 (M−H)$^+$.

2-(Azetidin-1-ylcarbonyl)-5-chloropyrazine

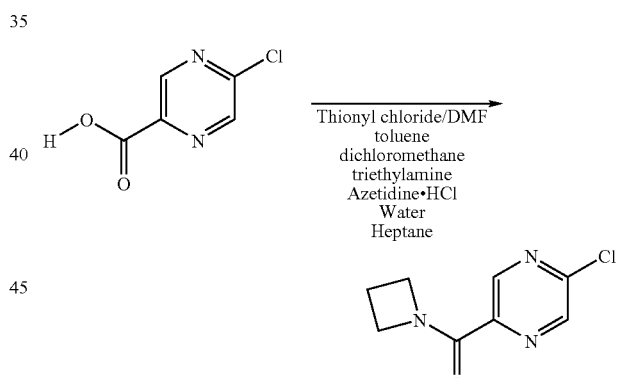

To a flask fitted with overhead stirrer, condenser, thermometer and nitrogen line was added 5-chloropyrazine-2-carboxylic acid (1.0 eq), DMF (0.069 eq) and toluene (5.52 vols) under a nitrogen atmosphere. The mixture was heated to 60-65° C., and thionyl chloride (1.5 eq) added drop-wise to the batch over approximately 2 hours. The thionyl chloride was washed into the flask with toluene (0.2 vols). The reaction mixture was heated at 60-65° C. for at least 4 hours, then cooled to 40-45° C. and distilled under vacuum, removing approximately 4.5 vol distillates, and distilling to a final volume of 3.2 vols. Toluene (10.6 vol) was added, and the mixture distilled under vacuum at 40-45° C., removing approximately 9.1 vol distillates, and distilling to a final volume of 4.7 vols. The mixture was then cooled to 20-25° C., and dichloromethane (10.6 vols) added. The mixture was cooled to 0-5° C. Meanwhile, to a second flask fitted with overhead stirrer, condenser, thermometer and nitrogen line was added azetidine hydrochloride (0.284 eq), dichloromethane (5.2 vols) under a nitrogen atmosphere. Triethylamine (2.57 eq) was added over at least 15 minutes maintaining the reaction temperature from 20-25° C., the triethylamine was washed into the flask with dichloromethane (0.13 vols), and the mixture cooled to −5° C. to −10° C. The acid chloride solution in the first flask was added to the second flask in portions maintaining the reaction temperature at −5° C. to −10° C. over a time period of 2-5 hours. The pH was tested and adjusted to pH>7 after the acid chloride addition. The reaction mixture was agitated for at least 30 minutes at −5° C. to −10° C. Water (10.6 vols) was added to the second flask and the temperature was allowed to increase to 20-25° C. The mixture was agitated for approximately 25 minutes and then the layers were separated. A 3.17% w/w solution (1.46 eq) of hydrochloric acid (prepared from 32% w/w hydrochloric acid and water) was added to the organic layer B keeping the batch temperature at 20-25° C. The mixture was agitated for 30 minutes at this temperature. The layers were separated, and the organic phase was treated with 26% w/w sodium chloride solution (approximately 8.9 vols) and the batch agitated at 20-25° C. for at least 15 minutes. The layers were separated and the organic layers was heated to reflux, and dichloromethane was removed by atmospheric distillation, distilling to a final volume of approximately 1-2 vols, collecting approximately 11.9 vols distillates. The resulting mixture was cooled to 20-25° C., and heptane (10.5 vols) added. The mixture was heated to reflux for 60 minutes, and then cooled to 90-100° C. The hot solution was filtered through a filter containing 10% w/w of activated charcoal into a clean dry vessel. The filter was washed with heptane (0.43 vols) and the solution cooled to 20-25° C. over at least 2 hours. The resulting crystallised slurry was filtered, and the solid washed with pentane (0.94 vols). After drying in the vacuum oven at 40° C. overnight, the desired product was obtained as a solid (corrected yield 65-78%). $^1$H NMR δ (400 MHz CDCl$_3$): 2.35-2.42 (2H, m), 4.26 (2H, t), 4.67 (2H, t), 8.52 (1H, d), 9.09 (1H, d); m/z 198 (M+H)$^+$.

tert-Butyl (5-methylpyrazin-2-yl)carbamate

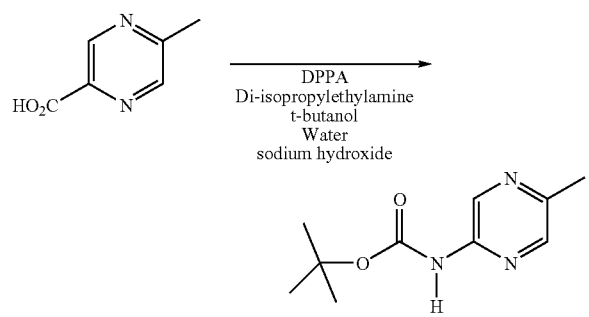

To a flask fitted with overhead stirrer, condenser, thermometer and nitrogen line was added 5-methylpyrazine-2-carboxylic acid (1.0 eq), tert-butanol (3.5 vols) and di-isopropylethylamine (1.5 eq) under a nitrogen atmosphere. The mixture was heated to 82° C., then diphenylphosphorylazide (1.0 eq) was added over a time period of 5-14 hours, maintaining the temperature of the reaction mixture at approximately 82° C. The reaction mixture was stirred for at least 1.5 hours, and then cooled to approximately 60° C. A solution of 4% w/w sodium hydroxide (1.75 eq) was added over a period of 2 hours. The mixture was cooled to 15° C. over at least 5 hours then held at 15° C. for 3 hours. The batch was then filtered, and the solid slurry washed with water (2 vols). The batch was again slurry washed with water (2 vols). After drying at 55-60° C. overnight, the desired product was obtained as a solid (corrected yield 56-63%). $^1$H NMR δ (400 MHz CDCl$_3$): 9.18 (s, 1H), 8.17 (bs, 1H), 8.11 (s, 1H), 2.51 (s, 3H), 1.56 (s, 9H)

5-Methylpyrazin-2-amine

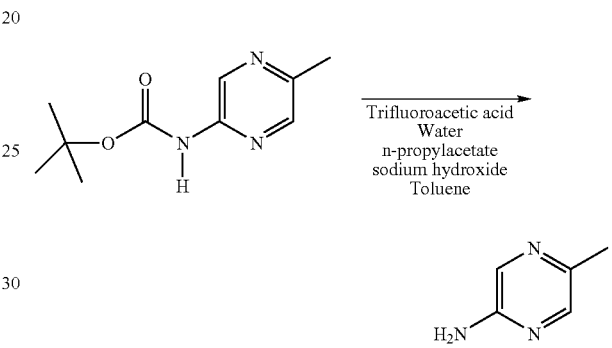

To a flask fitted with overhead stirrer, condenser, thermometer and nitrogen line was added tert-butyl (5-methylpyrazin-2-yl)carbamate (1.0 eq), and water (6.85 vols). The mixture was heated to 70° C. and trifluoroacetic acid (TFA) (1.2 eq) was added slowly drop-wise over 90-120 minutes. Water (0.22 vols) was added to wash the TFA into the flask. The reaction mixture was heated at 65-75° C. for at least 30 minutes, and then cooled to 15-25° C. Then 32% w/w sodium hydroxide (1.30 eq) was added drop-wise over 30-60 minutes maintaining the reaction temperature between 15-40° C. Water (0.22 vols) was added to wash the sodium hydroxide into the flask. N-Propylacetate (7.0 vols) was added and the mixture agitated for 45 minutes at 20° C. The layers were separated, the organic layer was retained and the aqueous layer was returned to the flask. N-Propylacetate (7.0 vols) was added and the mixture agitated for 45 minutes at 20° C. The layers were separated, the organic layer was retained and the aqueous layer was returned to the flask. This process was repeated twice. The combined organic layers were filtered through a filter containing silica (20% w/w) into a clean dry flask. The mixture was heated to 40° C. and then vacuum distilled to a final volume of 1.0-1.33 vols. Toluene (3.0 vols) was added, and the vacuum distillation continued at 40° C. to a final volume of 1.0-1.33 vols. This process was repeated twice. The resulting mixture was cooled to 5° C., and agitated for 1 hour at this temperature then filtered, washed with toluene (0.3 vols) at 0-5° C. The batch is slurry washed with toluene (1.0 vol) at 0-5° C. After drying at 45° C. overnight, the desired product was obtained as a solid (corrected yield typically 75%). ¹H NMR δ (400 MHz CDCl₃): 7.92 (s, 1H), 7.87 (s, 1H), 4.6 (bs, 2H), 2.40 (s, 3H)

Preparation of methyl 3-{[5-(azetidin-1-ylcarbonyl)pyrazin-2-yl]oxy}-5-[(1S)-2-methoxy-1-methylethoxy]benzoate

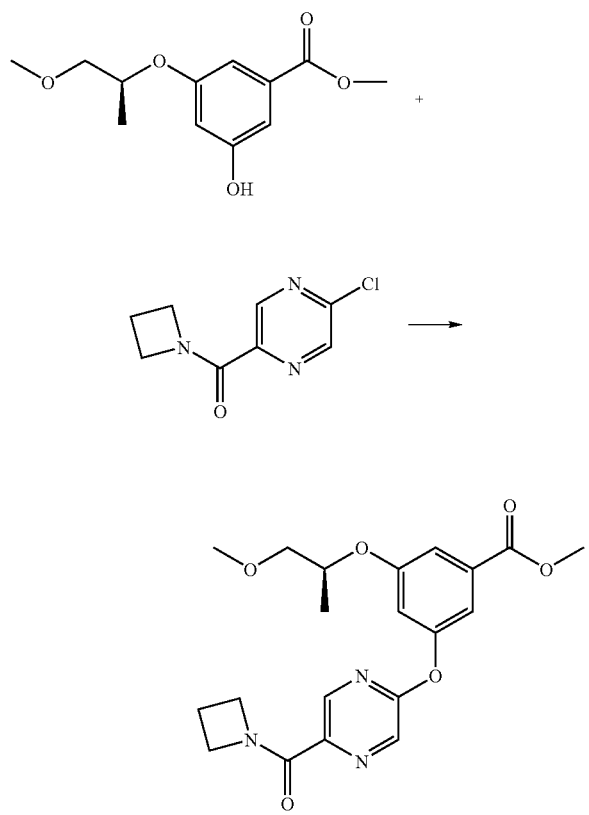

To a flask fitted with overhead stirrer, condenser, thermometer and nitrogen line was added methyl 3-hydroxy-5-[(1S)-2-methoxy-1-methylethoxy]benzoate (1.0 eq), 2-(azetidin-1-ylcarbonyl)-5-chloropyrazine (1.05 eq), cesium carbonate (1.5 eq) and dimethylsulfoxide (10 vols) under a nitrogen atmosphere. The contents of the flask were heated to 45° C. for 1.5 hours, then cooled to 22° C. Ethyl acetate (6 vols) and water (6 vols) were added to the flask, the mixture was agitated for 15 minutes, then the layers were separated. Water (3 vols) was added to the organic layer, the batch agitated for 15 minutes, then the layers were separated. This process was repeated with water (3 vols) then saturated brine (6 vols), then with water (6 vols). The organic layer was evaporated on the rotary evaporator to yield the title compound as an oil (93% yield corrected for assay). ¹H NMR δ (400 MHz) DMSO: 8.62 (s, 1H), 8.50 (s, 1H), 7.34 (s, 1H), 7.30 (s, 1H), 7.17 (s, 1H), 4.68-4.64 (m, 1H), 4.54-4.49 (t, 2H), 4.07-4.03 (t, 2H), 3.81 (s, 3H), 3.49-3.41 (m, 2H), 3.25 (s, 3H), 2.29-2.22 (m, 2H), 1.20-1.18 (d, 3H).

3-{[5-(Azetidin-1-ylcarbonyl)pyrazin-2-yl]oxy}-5-[(1S)-2-methoxy-1-methylethoxy]-N-(5-methylpyrazin-2-yl)benzamide

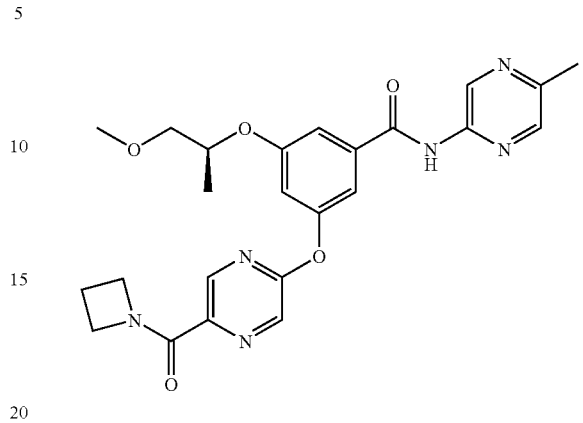

To a flask fitted with overhead stirrer, condenser, thermometer and nitrogen line was added 3-{[5-(azetidin-1-ylcarbonyl)pyrazin-2-yl]oxy}-5-[(1S)-2-methoxy-1-methylethoxy] benzoic acid (1.0 eq), and acetonitrile (10 vols) followed by pyridine (3 eq) under a nitrogen atmosphere. Thionyl chloride (1.2 eq) as a solution in acetonitrile (0.225 vols) was added slowly, drop-wise via syringe pump over at least 2 hours. 5-Methylpyrazin-2-amine (1.2 eq) was added to the mixture as a solid. After 2.5 hours the reaction was quenched by adding toluene (10 vols) and 1.0M sodium carbonate solution (2.5 eq). The layers were separated. The organic layer was retained in the flask, then 1.0M hydrochloric acid (1.94 eq) was added. The mixture was agitated for 15 minutes then separated. The organic layer was washed with two aliquots of water (5 vols) then the solvent was removed on the rotary evaporator. Toluene (5 vols) was added to the residue, and warmed to 45° C. Isohexane (1.7 vols) was added, the mixture was seeded, and allowed to cool to ambient temperature overnight. The mixture was cooled to 0° C. for 4 hours, and then cooled to −10° C. for 3 hours. The solid was isolated by filtration then washed with isohexane (2.5 vols). After drying in the vacuum oven at 40° C. overnight, the desired product was obtained as a solid (corrected yield 85%).

2-(Azetidin-1-ylcarbonyl)-5-chloropyrazine

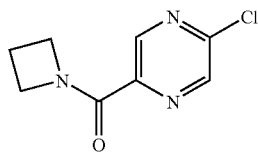

To a flask fitted with overhead stirrer, condenser, thermometer and nitrogen line was added 5-chloropyrazine-2-carboxylic acid (1.0 eq), tetrabutylammonium chloride (0.011 eq) and toluene (4 vols) under a nitrogen atmosphere. The mixture was heated to 70-75° C., and thionyl chloride (1.35 eq) added drop-wise over approximately 1 hours. The thionyl chloride was washed into the flask with toluene (1 vol). The mixture was heated at 70-75° C. for at least 4 hours, then cooled to 50±5° C. Toluene (5.3 vols) was added, and the mixture vacuum distilled at 50±5° C. (100 mbar), removing approximately 5.3 vol distillates, and distilling to a final volume of 5 vols. This process was repeated. The resulting mixture was then cooled to 20-25° C. Toluene (8.93 vols) was added, and the batch agitated at 50±5° C. to give an acid chloride solution.

Meanwhile, to a second flask was added azetidine hydrochloride (1.05 eq), toluene (6.07 vols), and a solution of potassium carbonate (1.24 eq) in water (6.07 vols). The resulting mixture was agitated at 20±5° C. for at least 15 minutes, then the layers were separated. The aqueous layer was returned to the flask, and toluene (6.07 vols) was added. The mixture was agitated at 20±5° C. for at least 15 minutes, then the layers were separated. The aqueous layer was returned to the flask, and potassium carbonate (1.24 eq) and toluene (6.07 vols) were added. The mixture was agitated for at least 30 minutes The acid chloride solution in the first flask was added to the mixture in the second flask in portions maintaining the reaction temperature at 20±5° C. over a time period of at least 20-60 minutes. The reaction mixture was agitated for at least 30 minutes at 20±5° C. and then filtered, the filter was washed with toluene (0.17 vol) and then the layers were separated. The lower aqueous phase was separated off and discarded. Water (6.07 vols) was added to the second flask and the mixture was agitated at 20±5° C. for approximately 15 minutes and then allowed to separate. The lower aqueous phase was separated off and discarded. A 5% w/w solution of hydrochloric acid (1.5 eq) (prepared from 32% w/w hydrochloric acid and water was added to the organic layer keeping the batch temperature at 20±5° C. The mixture was agitated for 15 minutes at this temperature then the layers were separated and the lower aqueous layer was discarded. 25% w/w Sodium chloride solution (approximately 6 vols) was added to the organic layer and the mixture agitated at 20-25° C. for at least 15 minutes. The layers were separated and the aqueous layer was discarded. The organic layer was heated to 50±5° C., and vacuum distilled to a final volume of 4.5 vols, collecting 15.2 vols distillate. Active charcoal (11% w/w) and heptane (12.8 vols) were added, and the mixture agitated at 90-100° C. for at least 1 hour. The mixture was filtered to clean dry vessel keeping the reaction temperature above 70° C. Heptane (1.16 vols) was used to wash the mixture into the filter. The mixture was cooled to 55-60° C., seeded with 2-(azetidin-1-ylcarbonyl)-5-chloropyrazine and cooled to 15-20° C. over at least 3 hours. The crystallised slurry was filtered, and the solid washed with 140-155 petroleum ether (1.45 vols). The solid was washed with 140-155 petroleum ether (1.45 vols). After drying in the vacuum oven at 40° C. overnight, the desired product was obtained as a solid corrected yield 65-78%).

Benzyl (5-methylpyrazin-2-yl)carbamate

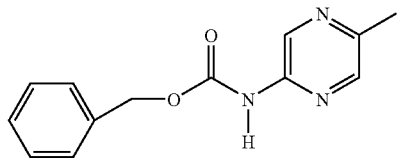

To a flask fitted with overhead stirrer, condenser, thermometer and nitrogen line was added 5-methylpyrazine-2-carboxylic acid (1.0 eq), toluene (2.5 vols) and di-isopropylethylamine (1.50 eq) under a nitrogen atmosphere. The mixture was vacuum distilled at a batch temperature of 50° C., distilling to a final volume of 2 vols. The batch was sampled to ensure the water content was <0.1% w/w, then cooled to 15±2° C., and diphenylphosphorylazide (1.00 eq) was added over a time period of 5-6 hours, maintaining the temperature of the reaction mixture at 15±2° C. The mixture was stirred for a further 1.5 hours. Meanwhile to a second flask was added benzyl alcohol (3.00 eq) and toluene (11 vols). The mixture was azeotropically dried to a volume of 10 vols. The contents of the second flask were sampled to ensure the water content was <0.1% w/w, then heated to 85-90° C. The contents of the first flask were added slowly to the contents of the second flask over approximately 2 hours, maintaining the reaction temperature at approximately 85° C. The reaction mixture was stirred for 1 hour at 85° C., then cooled to 20° C. 5% w/w Sodium hydroxide solution (1.75 eq) was added slowly over 1 hour, the mixture cooled to 5° C., agitated at 5° C. for 1 hour, then filtered. The isolated solid was washed sequentially with water (2 vols), then methanol (2 vols). After drying in the vacuum oven at 40° C. overnight, the desired product was obtained as a solid (corrected yield 78-85%). $^1$H NMR (400 MHz, CDCl$_3$): 9.41 bs (1H), 9.24 s (1H), 7.87 s (1H), 7.39-7.41 m (5H), 5.22 s (2H), 2.31 s (3H)

5-Methylpyrazine-2-amine

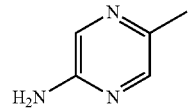

To a flask fitted with overhead stirrer, condenser, thermometer and nitrogen line was added benzyl(5-methylpyrazin-2-yl)carbamate (1.0 eq), palladium on carbon catalyst E196 (3% w/w palladium on dry basis)), sodium hydroxide (0.01 eq)—and methanol (5 vols) under a nitrogen pad. The reaction was de-gassed by pressurising and releasing under nitrogen, then charged with hydrogen to atmospheric pressure and the reaction agitated at 20±5° C. for at least 3 hours. Activated charcoal (Norit SX Ultra) (5% wt charge) was added to the flask, the mixture was agitated for at least 30 minutes at 20±5° C., then filtered through a 0.45 micron filter. The filter was rinsed with methanol (1 vol) then the mother liquors allowed to stir at 15° C. under an atmosphere of 6% oxygen/94% nitrogen for up to 24 hours (alternatively an atmosphere of 1% oxygen/99% nitrogen was used), then re-filtered through the 0.45 micron filter. The mother liquors were vacuum distilled at 45° C. to a final volume of 1.5 vols. Toluene (1.5 vols) was added and the mixture vacuum distilled at 45° C. to a final volume of 1.5 vols. This process was repeated with further toluene (0.5 vols) then the resulting mixture was cooled to 5° C. and filtered. The solid was washed with toluene (1 vol). The solid was washed with toluene (1 vol). After drying in the vacuum oven at 40° C. overnight, the desired product was obtained as a solid (corrected yield 65-78%).

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide) (as form 6)

A

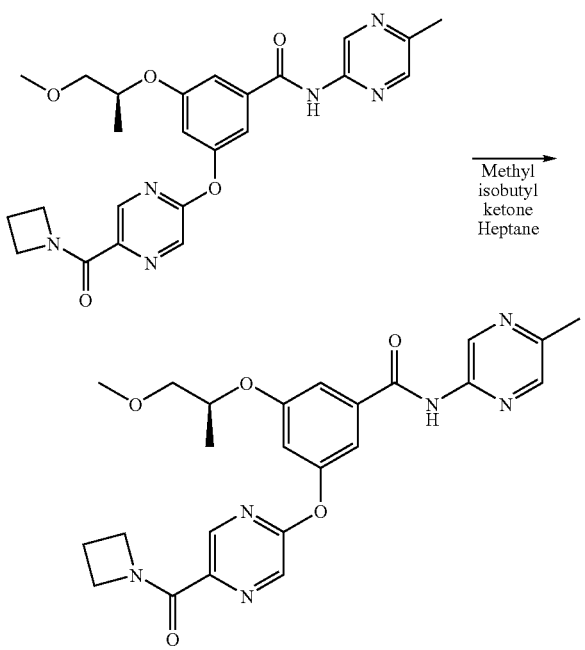

To a flask fitted with thermometer, condenser, overhead stirrer and nitrogen line was added 3-{[5-(azetidin-1-ylcarbonyl)pyrazin-2-yl]oxy}-5-[(1S)-2-methoxy-1-methylethoxy]-N-(5-methylpyrazin-2-yl)benzamide (1.0 eq) and methyl isobutyl ketone (6.7 vols) under a nitrogen atmosphere. The batch was heated to 60° C. and filtered into another flask. The mixture was cooled to 45° C., and then seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide) (form 6) (0.075% w/w). The mixture was held at 45° C. for 6 hours, then subjected to a stepped cooling profile. The mixture was cooled to 40° C. and held for 6 hours, then cooled to 35° C. and held for 6 hours, then cooled to 30° C. and held for 6 hours, then cooled to 20° C. and held for 6 hours, then cooled to 10° C. and held for 3 hours. To the mixture n-heptane was then added slowly over a period of 2 hours maintaining the mixture at 10° C., following the addition the mixture was held for a further 1 hour at 10° C. The mixture was then cooled to 0° C. and held for 6 hours before being filtered. The solid was washed with (2 vols) methyl isobutyl ketone/n heptane mixture (9/1 volume ratio) pre-chilled to 0° C. The solid was dried at 40° C. until the solvent level was <0.5% w/w. After drying in the vacuum oven at 40° C. overnight, the title compound was obtained as a solid (corrected yield 85%).

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide) (as form 6)

B

Crude 3-{[5-(azetidin-1-ylcarbonyl)pyrazin-2-yl]oxy}-5-[(1S)-2-methoxy-1-methyl-ethoxy]-N-(5-methylpyrazin-2-yl)benzamide) was suspended in 6.7 rel vol. of methyl isobutyl ketone (MIBK). The mixture was heated to 70° C. to dissolve the solid. Once the solid has dissolved the mixture was filtered to generate a Pures envelope. The solution was then cooled to 45° C., seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide) Form VI and held for 4 hours at 45° C. The mixture was then cooled using a stepped cooling profile (cooled to 40° C. and held for 4 hours, cooled to 35° C. and held for 6 hours, cooled to 30° C. and held for 6 hours cooled to 20° C. and held for 3 hours, cooled to 10° C. and held for 3 hours and cooled to 0° C. and held for 3 hours). The mixture was then subjected to a number of temperature cycles to break up the crystal agglomerates. The mixture was heated from 0° C. to 30° C. at 0.5° C./min, and held at 30° C. for 2 hours and then cooled back to 0° C. at 0.1° C./min and held at for 3 hours. This temperature cycle was repeated a further 3 times. After an in-process control to confirm the formation of the desired physical form, the mixture was filtered and washed with 50/50 v/v MIBK/n-heptane. The solid was dried under vacuum at 60° C. until constant weight was attained. Yield=75-82%. Washing may be also performed with mixtures of n-heptane and MIBK containing a higher or lower relative amount of MIBK.

Formation of Form 6 from a Slurry of Forms 1 and 4

An approximately 1:1 mixture of forms 1 and 4 (30 mg total) was slurried in 50-300 μl of IPA and held at elevated temperatures for a number of days. Substantially complete conversion into Form 6 (as identified by XRPD) was obtained as follows:

35° C.: 8 days
40° C.: 11 days (conversion not complete but sample was not kept moist all of the time and was at room temperature for 3 of the 11 days)
45° C.: 11 days (not tested before this timepoint)
50° C.: 11 days (not tested before this timepoint).

The invention claimed is:

1. A crystalline form of the compound of formula (I)

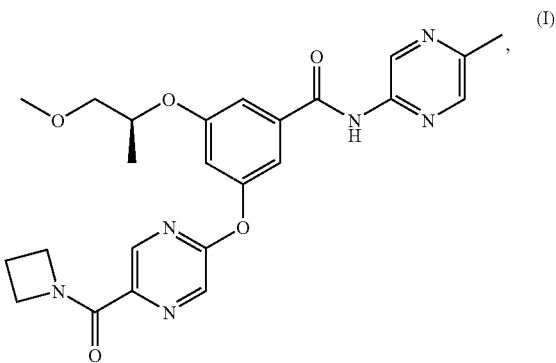

having an X-ray powder diffraction pattern with peaks at d-value (Å) 11.8 and 5.7.

2. The crystalline form of claim 1 having an X-ray powder diffraction pattern with peaks at d-value (Å) 11.8, 10.5, 6.4, 5.9 and 5.7.

3. The crystalline form of claim 1 having an X-ray powder diffraction pattern with peaks at d-value (Å) 11.8, 10.5, 6.4, 5.9, 5.7 and 3.75.

4. The crystalline form of claim 1 having an X-ray powder diffraction pattern with peaks at d-value (Å) 11.8, 10.5, 8.2, 6.4, 5.9, 5.7, 5.2, 3.75 and 3.44.

5. The crystalline form of claim 1 having an X-ray powder diffraction pattern as shown in FIG. 1.

6. A pharmaceutical composition comprising the crystalline form of claim 1, together with a pharmaceutically acceptable carrier.

7. A process for the manufacture of a pharmaceutical composition of claim 6 which comprises admixing the crystalline form of the compound of formula (I), together with the pharmaceutically acceptable carrier.

* * * * *